US006701341B1

(12) United States Patent
Wu et al.

(10) Patent No.: US 6,701,341 B1
(45) Date of Patent: Mar. 2, 2004

(54) SCALABLE REAL-TIME ULTRASOUND INFORMATION PROCESSING SYSTEM

(75) Inventors: Anthony Wu, San Jose, CA (US); Shengtz Lin, Cupertino, CA (US); Ali Moayer, Castro Valley, CA (US); Pin Yu, Palo Alto, CA (US)

(73) Assignee: U-Systems, Inc., Los Altos, CA (US)

( * ) Notice: Subject to any disclaimer, the term of this patent is extended or adjusted under 35 U.S.C. 154(b) by 0 days.

(21) Appl. No.: 09/449,095

(22) Filed: Nov. 24, 1999

Related U.S. Application Data

(63) Continuation-in-part of application No. 09/224,635, filed on Dec. 31, 1998, now Pat. No. 6,547,730.

(51) Int. Cl.[7] ............................................. G06F 15/16

(52) U.S. Cl. ....................... 709/200; 709/200; 709/101; 709/106; 709/201; 709/205; 128/915; 128/916; 600/437; 600/442; 600/447; 600/453; 600/345; 600/502; 600/810; 600/348

(58) Field of Search ............................... 709/101, 106, 709/201, 205

(56) References Cited

U.S. PATENT DOCUMENTS

| 4,853,875 | A | | 8/1989 | Brown |
| 4,962,381 | A | * | 10/1990 | Helbig, Sr. |
| 5,295,485 | A | | 3/1994 | Shinomura et al. |
| 5,315,700 | A | * | 5/1994 | Johnson et al. |
| 5,353,220 | A | | 10/1994 | Ito et al. |
| 5,483,963 | A | | 1/1996 | Butler et al. |

(List continued on next page.)

OTHER PUBLICATIONS

CF1 User's Manual: "PicoDOS Ping–Pong Buffer Functions", May 1999 http://www.persistor.com/doc/CF1/Docs/html/PersistorCF1UsersManual/sections/picodos/pico_pp-b.htm.*

(List continued on next page.)

*Primary Examiner*—Hosain Alam
*Assistant Examiner*—Young N Won
(74) *Attorney, Agent, or Firm*—Cooper & Dunham LLP; Ivan S. Kavrukov

(57) ABSTRACT

An ultrasound information processing system is disclosed in which ultrasound image data is packetized into ultrasound information packets and routed to one or more of a plurality of processors for performing image processing operations on the ultrasound image data, the ultrasound information packets being routed according to entries in a host-programmable routing table. A common distribution bus is coupled between packetizing circuitry and dedicated input buffers corresponding to each processor for distributing the ultrasound information packets, and a common output bus to is used to transfer processed image data from the processors to an output device. The disclosed ultrasound information processing system architecture allows for a high throughput rate for accommodating real-time image processing operations, while also allowing for ready programmability and upgradability. Advantageously, the disclosed ultrasound information processing system may be readily upgraded by coupling additional processors to the common distribution bus and the common output bus and by reprogramming the routing table to include the additional processors as destinations for the ultrasound information packets. The disclosed ultrasound information processing system architecture also provides for added field reliability by providing for an optional spare processor coupled to the common distribution bus and the common output bus, wherein upon detection of a failure of one of the existing processors, the optional spare processor may be loaded with a copy of a program being run by the failing processor and the routing table may by automatically modified to redirect ultrasound data packets from the failing processor to the spare processor.

14 Claims, 18 Drawing Sheets

U.S. PATENT DOCUMENTS

| | | | |
|---|---|---|---|
| 5,492,125 A | | 2/1996 | Kim et al. |
| 5,528,302 A | * | 6/1996 | Basoglu et al. |
| 5,590,658 A | | 1/1997 | Chiang et al. |
| 5,590,659 A | * | 1/1997 | Hamilton et al. |
| 5,603,323 A | | 2/1997 | Pflugrath et al. |
| 5,630,101 A | | 5/1997 | Sieffert |
| 5,709,206 A | | 1/1998 | Teboul |
| 5,709,209 A | * | 1/1998 | Friemel et al. |
| 5,715,823 A | | 2/1998 | Wood et al. |
| 5,778,177 A | | 7/1998 | Azar |
| 5,795,297 A | | 8/1998 | Daigle |
| 5,802,316 A | * | 9/1998 | Ito et al. |
| 5,838,592 A | | 11/1998 | Spratt |
| 5,851,186 A | | 12/1998 | Wood et al. |
| 5,853,367 A | | 12/1998 | Chalek et al. |
| 5,885,218 A | | 3/1999 | Teo et al. |
| 5,935,072 A | * | 8/1999 | Hamilton et al. |
| 5,971,923 A | * | 10/1999 | Finger |
| 5,997,478 A | | 12/1999 | Jackson et al. |
| 6,101,407 A | | 8/2000 | Groezinger |
| 6,210,334 B1 | * | 4/2001 | Philips |
| 6,254,542 B1 | * | 7/2001 | Hamilton et al. |
| 6,272,522 B1 | * | 8/2001 | Lin et al. |
| 6,388,687 B1 | * | 5/2002 | Brackett et al. |

OTHER PUBLICATIONS

Texas Instruments, Inc., http://www.ti.com.

Sheldon, *The Encyclopedia of Networking*, McGraw–Hill (1997).

James A. Zagzebski, *Essentials of Ultrasound Physics* (1996) (title page and table of contents).

* cited by examiner

| TYPE 1702 | ZONE/ ENSEMBLE 1704 | LINE 1706 | ROUTED DSP 1708 | ... | INTRABUFFER ADDRESS 1 1710 | INTRABUFFER ADDRESS 2 1712 |
|---|---|---|---|---|---|---|
| 001 | 1 | 61 | 1000 | ... | (16-BIT ADDRESS) | NULL |
| 001 | 1 | 62 | 1100 | ... | (16-BIT ADDRESS) | (16-BIT ADDRESS) |
| 001 | 1 | 63 | 1100 | ... | (16-BIT ADDRESS) | (16-BIT ADDRESS) |
| 001 | 1 | 64 | 1100 | ... | (16-BIT ADDRESS) | (16-BIT ADDRESS) |
| 001 | 1 | 65 | 1100 | ... | (16-BIT ADDRESS) | (16-BIT ADDRESS) |
| 001 | 1 | 66 | 0100 | ... | (16-BIT ADDRESS) | NULL |
| 001 | 1 | 125 | 0100 | ... | (16-BIT ADDRESS) | NULL |
| 001 | 1 | 126 | 0110 | ... | (16-BIT ADDRESS) | (16-BIT ADDRESS) |
| 001 | 1 | 127 | 0110 | ... | (16-BIT ADDRESS) | (16-BIT ADDRESS) |
| 001 | 1 | 128 | 0110 | ... | (16-BIT ADDRESS) | (16-BIT ADDRESS) |
| 001 | 1 | 129 | 0110 | ... | (16-BIT ADDRESS) | (16-BIT ADDRESS) |
| 001 | 1 | 130 | 0010 | ... | (16-BIT ADDRESS) | NULL |

SCALABLE REAL-TIME ULTRASOUND INFORMATION PROCESSING SYSTEM

CROSS-REFERENCE TO RELATED APPLICATIONS

This application is a continuation-in-part of U.S. patent application Ser. No. 09/224,635, entitled "Ultrasound Information Processing System," filed Dec. 31, 1998 U.S. Pat. No. 6,547,730, which is assigned to the assignee of the present invention, and which is hereby incorporated by reference into the present application.

FIELD OF THE INVENTION

The present invention relates to the field of ultrasound information processing systems. In particular, the present invention relates to an architecture for a low-cost, flexible, and scalable ultrasound information processing system capable of performing computationally intensive image processing algorithms in real time on ultrasound data.

BACKGROUND OF THE INVENTION

Ultrasound imaging systems are advantageous for use in medical diagnosis as they are non-invasive, easy to use, and do not subject patients to the dangers of electromagnetic radiation. Instead of electromagnetic radiation, an ultrasound imaging system transmits sound waves of very high frequency (e.g., 2 MHz to 10 MHz) into the patient and processes echoes reflected from structures in the patient's body to form two dimensional or three dimensional images. Many ultrasound information processing algorithms are known in the art, e.g., echo mode ("B mode") processing algorithms, motion mode ("M mode") processing algorithms, Doppler shift echo processing algorithms, color flow mode processing algorithms, and others.

In the design and development of an ultrasound information processing architecture, there have historically been tradeoffs among features directed to high data throughput (to allow for real-time image display image), flexibility (to accommodate various ultrasound clinical applications), scalability (for adapting a given ultrasound hardware architectures to differing field capacity requirements), and low cost of manufacture and maintenance. Generally speaking, the prior art ultrasound hardware architectures directed to higher data throughputs have had shortcomings in the areas of flexibility, scalability, and cost, while other prior art architectures directed to increased flexibility have had shortcomings in real-time data throughput and scalability.

FIG. 1 shows a block diagram of a conventional ultrasound information processing system 100 similar to a system disclosed in U.S. Pat. No. 5,492,125, "Ultrasound Signal Processing Apparatus," the contents of which are hereby incorporated by reference into the present disclosure. Ultrasound information processing system 100 comprises a system controller 102 for receiving and displaying user control information via a user interface 104. During operation, system control signals are output to an ultrasound front end comprising a transducer 106, a transmitter 108, and a beam-former 110. Transmitter 108 generates output signals to transducer 106 to define aperture, apodization, focus and steering of acoustic ultrasound signals into the target subject. Reflected signals from the subject being imaged are sensed by transducer 106 and captured as a patterned beam by beam-former 110.

In the system of FIG. 1, the captured signals are sent to a back end signal processing subsystem 112 in the form of digital echo signals, flow signals and/or Doppler signals according to various modes of operation. For purposes of the present disclosure, the captured signals are referred to herein as digital samples, it being understood that the physical significance of the digital samples will vary according to the mode of operation. The function of the back end signal processing subsystem is to process the digital samples and generate image data for output device 114.

FIG. 2 shows a diagram of a representative frame 200 of an ultrasound target with, respect to a transducer 202 for more particularly describing the digital samples being processed by the back end signal processing subsystem 112. In the example of FIG. 2 the transducer 202, which corresponds generally to the transducer 106 of FIG. 1, is a convex probe transducer with a 90 degree span. As shown in FIG. 2, the frame 200 comprises a set of scan lines 204 and a set of zones 206. In a typical ultrasound application, there may be up to 256 scan lines, and for each scan line there may be up to 1024 digital samples corresponding to ultrasound beam reflections. Each digital sample is typically 8 to 32 bits depending on the particular application. The scan lines 204 may be identified by their sequential position or by an angular position with respect to the center line of the transducer 202. Importantly, it is to be understood that the dimensions, resolutions, and other parameters disclosed herein are presented by way of example only to more clearly describe the features and advantages of the preferred embodiments disclosed infra, and are not intended to limit the scope of the preferred embodiments.

As known in the art, the frame 200 may also be divided axially (i.e., depthwise) into zones 206 for applications such as multi-zone focusing. In multi-zone focusing, acoustic ultrasound pulses may be sent and received in gated time windows focused to a particular zone for greater resolution in that particular zone. The number of zones 206 may vary greatly, with typical numbers being between 4 and 20 zones.

FIG. 3 shows a diagram of a representative frame 300 of an ultrasound target with respect to a flat probe transducer 302. The frame 300 also comprises scan lines 304 and zones 306 similar to the scan lines 204 and zones 206 of FIG. 2, respectively, except that the scan lines 304 may be indexed by distance offset (e.g., in centimeters) instead of angular offsets as in FIG. 2.

A problem arises in practical ultrasound systems when real-time ultrasound imaging is required, due to the high throughput rate required in real-time ultrasound imaging. For real-time ultrasound imaging systems, based on the typical parameters recited above with respect to FIGS. 2 and 3, using a digital sample resolution of 24 bits per sample and a desired frame rate of approximately 60 frames per second, the data throughput rate for the back end signal processing subsystem 112 would need to be as great as (24)(1024)(256)(60)=368 Mbps to permit real-time results. However, as described in Zagzebski, *Essentials of Ultrasound Physics* (1996), the contents of which are hereby incorporated by reference into the present disclosure, unprocessed ultrasound images display a variety of undesirable characteristics such as speckle, blur, blockiness and other adverse artifacts. To reduce the undesirable characteristics, and also to obtain further useful information from the ultrasound data, it is desirable to perform a variety of image processing algorithms on the ultrasound data prior to display such as speckle reduction, histogram equalization, contrast limited adaptive histogram equalization, edge detection, boundary enhancement, 2-D graphics, 3-D volume visualization, tissue characterization, image segmentation, perfusion measurements, and other algorithms. Additionally, as shown in U.S. Pat. 5,885,218, the contents of which are hereby incorporated by reference into the present disclosure, new spatial signal processing algorithms are continually being introduced for obtaining further useful information from the ultrasound data. Accordingly, there is a need for an ultrasound processing hardware platform capable of performing complex signal processing algorithms on ultrasound data while also being capable of sustaining the above very high throughput rate for real-time imaging.

U.S. Pat. No. 5,492,125 ("the '125 patent") is directed to the goal of an ultrasound signal processing apparatus having a back-end ultrasound processing subsystem that is more versatile and programmable. In contrast to prior systems presented therein containing multiple distinct special-purpose processor boards dedicated to a particular type of ultrasound processing (e.g., one processor board for Doppler processing, a different board for B-mode processing, etc.), the '125 patent discloses the use of a common pool of programmable multiprocessors such as multimedia video processors. However, in the '125 patent, the programmable multiprocessors access a shared memory through a crossbar switch. Although the apparatus of the '125 patent is adaptable to different image processing algorithms through a reprogramming of the multiprocessors, the crossbar switch introduces a bottleneck as the data rate is increased or where the input samples are presented in a random sequence, which hampers real-time ability when complex spatial image processing algorithms are needed. When a bottleneck is introduced, much of the processing capacity of the programmable multiprocessors goes unused. Because a large portion of the cost of any ultrasound information processing system usually lies in the "number-crunching" hardware such as the programmable multiprocessors, a cost-performance inefficiency results where this expensive hardware is either underused due to upstream bottlenecks in the system or is inefficiently used to rearrange to the order of the digital samples prior to performing image processing operations on the data.

U.S. Pat. No. 5,709,209 ("the '209 patent"), supra, is directed to the goal of higher throughput in a back-end ultrasound processing subsystem for real-time imaging in the various modes of ultrasound operations. The '209 patent discloses an embodiment employing a multiple digital signal processor (digital signal processor) approach with shared memory and a crossbar switch similar to the disclosure of the '125 patent and having similar limitations. The '209 patent also discloses an embodiment in which a plurality of identical processor boards are configured to receive data from a input bus in a "round-robin" approach, process the data, and output the results on an output bus separate from the input bus. However, the architecture of the latter '209 patent embodiment is deficient in a way which makes it less practical for real-world real-time ultrasound processing. As known in the art, scan lines from known transducer/beamformers are usually presented in a random sequence, and not in a sequential fashion by line number, to reduce extraneous reflections and clutter while still keeping up the frame rate. However, a "round-robin" approach of data stream distribution among the processor boards necessarily presupposes the arrival of scan line data in a sequential manner. Accordingly, the round-robin approach as disclosed in the '209 patent is not adapted for real-time processing of the ultrasound data in practical environments in which scan lines arrive at very high data rates in random sequence from the front end components of the ultrasound system.

Accordingly, it would be desirable to provide an ultrasound information processing system capable of performing complex spatial image processing algorithms on real-time ultrasound data streams.

It would be further desirable to provide an ultrasound information processing system that is flexible and readily adaptable to various ultrasound clinical applications.

It would be still further desirable to provide an ultrasound information processing system that is scalable, for adapting the system to different differing capacity requirements and budgets, and for allowing easy upgrades of an existing system to more powerful configurations, with the speed of the overall system being limited by the raw processing capacity of its image processors, rather than by bottlenecks formed by the hardware that feeds the data to the image processors.

It would be still further desirable to provide an ultrasound information processing system that is capable of redundancy, such that operation can continue if a key processing component fails in critical environments.

It would be still further desirable to provide an ultrasound information processing architecture that can be built at low cost, wherein key ultrasound processing components can be implemented using commercial off the shelf hardware.

It would be still further desirable to provide a real-time, flexible, upgradable, adaptable, robust, and low-cost ultrasound information processor that is capable of implementing complex spatial signal processing algorithms in real time on scan line data that is presented in random order from front end ultrasound components.

SUMMARY OF THE INVENTION

In accordance with a preferred embodiment, an ultrasound information processing system is provided in which ultrasound image data is packetized into ultrasound information packets and routed to one or more of a plurality of processors for performing image processing operations on the ultrasound image data, the ultrasound information packets being routed according to entries in a host-programmable routing table. A common distribution bus is coupled between packetizing circuitry and dedicated input buffers corresponding to each processor for distributing the ultrasound information packets. A common output bus is used to transfer processed image data from the processors to an output device. Advantageously, the ultrasound information processing system throughput is high enough to accommodate real-time image processing operations, while the system is also flexible and can be readily upgraded by coupling additional processors to the common distribution bus and the common output bus and by reprogramming the routing table to include the additional processors as destinations for the ultrasound information packets.

In a preferred embodiment, the ultrasound information processing system includes packetizing circuitry for receiving ultrasound data derived from an ultrasound transducer and for organizing the ultrasound data into ultrasound information packets. The ultrasound data comprises digital samples corresponding to locations in an ultrasound frame, the ultrasound frame comprising a plurality of lines. The ultrasound information packets comprise location information including a line number and a payload comprising the digital samples corresponding the location information. The ultrasound information processing system includes a plurality of processors for performing image processing operations on the ultrasound data, and a routing table for storing routing data that associates each ultrasound information packet with a subset of the processors according to the location information in that ultrasound information packet. Control circuitry routes each ultrasound information packet to its associated subset of processors according to the routing data, and an output bus transfers processed image data from the processors to an output device.

Also in a preferred embodiment, the control, circuitry routes each ultrasound information packet to its associated subset of processors by instructing the input buffers associated with that subset of processors to read from the distribution bus when the ultrasound information packet is present on the distribution bus. Each input buffer comprises a ping-pong buffer having a first memory bank and a second memory bank, the ping-pong buffer being adapted to load image data into the first memory bank from the distribution bus while the processor associated with that input buffer is accessing and processing image data from the second memory bank, the ping-pong buffer being likewise adapted to load image data into the second memory bank from the distribution bus while the processor is accessing and processing image data from the first memory bank. Preferably, the processor accesses the image data from the input buffer memory banks in a direct memory access (DMA) fashion. When an ultrasound information packet arrives at the input, buffer, it is placed in proper order within the ultrasound frame as dictated by an intrabuffer destination address stored in the routing table. In this manner, the processors are efficiently used and valuable CPU cycles are not wasted waiting for a frame of data to load or by rearranging the digital samples prior to the image processing operations. A host computer is used for overall management and control, the host computer being coupled to the control circuitry, to each of the processors, and to the routing table by means of high-speed serial links. The host computer is used to download image processing programs into the processors and routing data into the routing table.

In another preferred embodiment, the disclosed ultrasound information processing system architecture may be adapted for increased field reliability of the overall system. In particular, a spare processor may be coupled to the common distribution bus and the common output bus, and the host computer is adapted to monitor the active processors for a failure condition. Upon detection of a failure of one of the active processors, the hot computer loads the spare processor with a copy of a program being run by the failing processor, and the host computer modifies the routing table to redirect ultrasound data packets from the failing processor to the spare processor.

The ability to hot-swap a failing processor with a replacement processor is one of several advantages of an ultrasound information system in accordance with the preferred embodiments, other advantages including: high data throughput through the use of multiple processors, separate distribution and output buses, and a pipelined data flow with DMA buffer access by the processor; increased flexibility and the ability to process randomly arriving line data through the use of a host-programmable routing table; and better cost-performance efficiency through the use of a scalable architecture.

BRIEF DESCRIPTION OF THE DRAWINGS

FIG. 17 shows sections of routing data that may be loaded into a routing table for allowing digital samples corresponding to sector overlap regions to be processed by more than one processor in accordance with a preferred embodiment;

DETAILED DESCRIPTION

Figure 4:
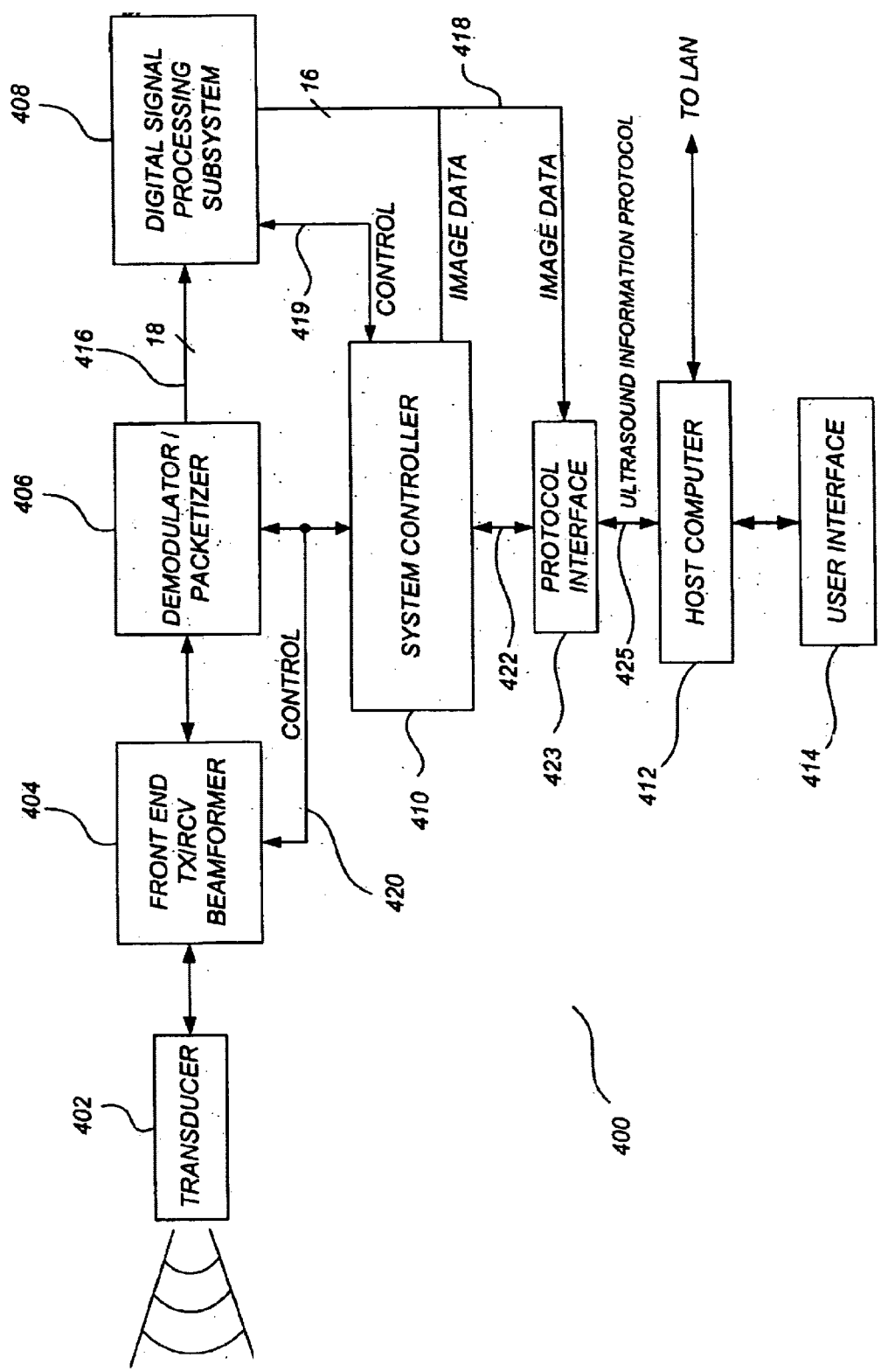
FIG. 4 shows a diagram of an ultrasound information processing system in accordance with a preferred embodiment.

FIG. 4 shows a diagram of an ultrasound information processing system 400 in accordance with a preferred embodiment. Ultrasound information processing system 400 comprises a transducer 402, a front end transmit/receive beamformer 404, a demodulator/packetizer 406, a digital signal processing subsystem 408, a system controller 410, a host computer 412, and a user interface 414. Using known methods, transducer 402 comprises an array of transducer elements that generates focused acoustic signals responsive to signals generated by front end transmit/receive beamformer 404. Also using known methods, transducer 402 generates electrical signals responsive to received echoes that are processed by front end transmit/receive beamformer 404, which in turn transmits digital RF samples to demodulator/packetizer 406 for further processing.

Demodulator/packetizer 406 comprises demodulating circuitry that receives the digital RF samples from front end transmit/receive beamformer 404 and generates digital samples using known methods. However, in accordance with a preferred embodiment, demodulator/packetizer 406 further comprises packetizing circuitry that generates ultrasound information packets from the digital samples, and transmits the ultrasound information packets to digital signal processing subsystem 408 over a bus 416. Advantageously, the packetizing of the digital samples into ultrasound information packets in accordance with the preferred embodiments provides for fast, flexible, real-time processing by digital processing subsystem 408 as described infra. Processed image data is then transferred from digital processing subsystem 408 to a protocol interface 423 over an output bus 418. In a preferred embodiment, protocol interface 423 is an IEEE 1394 interface that translates parallel image data from output bus 418 onto an isochronous channel of a high-speed serial bus 425. High-speed serial bus 425 is a modified IEEE 1394 bus in which image content is sent one-way from protocol interface 423 to host computer 412 over the isochronous channel, and wherein commands are sent both ways over an asynchronous channel. In a preferred embodiment, commands and responses transmitted by high-speed serial bus 425 are in accordance with the ultrasound information exchange protocol disclosed in application Ser. No. 09/224,635, supra.

As shown in FIG. 4, system controller 410 sends ultrasound processing commands over a front end bus 420 to front end transmit/receive beamformer 404 and demodulator/packetizer 406, and to digital processing subsystem 408 over a control link 419. Although the front end bus 420 may be physically implemented using any of a variety of bus types, it is found that a modified ISA bus having a bandwidth of 12 MWords/s at 16 bits/Word is suitable for most practical applications.

System controller 410 is coupled to protocol interface 423 over a link 422. Protocol interface 423 translates the commands from link 422 onto the asynchronous channel of the high-speed serial bus 425 for transfer to and from host computer 412. Thus, protocol interface 423 serves the function of both translating commands from system controller 410 onto the asynchronous channel of high-speed serial bus 425, as well as translating image data from output data bus 418 onto the isochronous channel of high-speed serial bus 425, according to the ultrasound information protocol described U.S. patent application Ser. No. 09/224,635, supra. Advantageously, the ultrasound information protocol may be used for communicating among a variety of ultrasound information devices.

System controller 410 performs several functions including receiving ultrasound information exchange protocol commands and parameters from host computer 412, transmitting control signals over control link 419, and transmitting control signals over front end bus 420. Among the control signals transmitted are scan sequences that dictate a scan sequence to front end transmit/receive beamformer 404, as well as overall data flow control signals to the transmit/receive beamformer 404, the demodulator/packetizer 406, and the digital processing subsystem 408.

Figure 1:
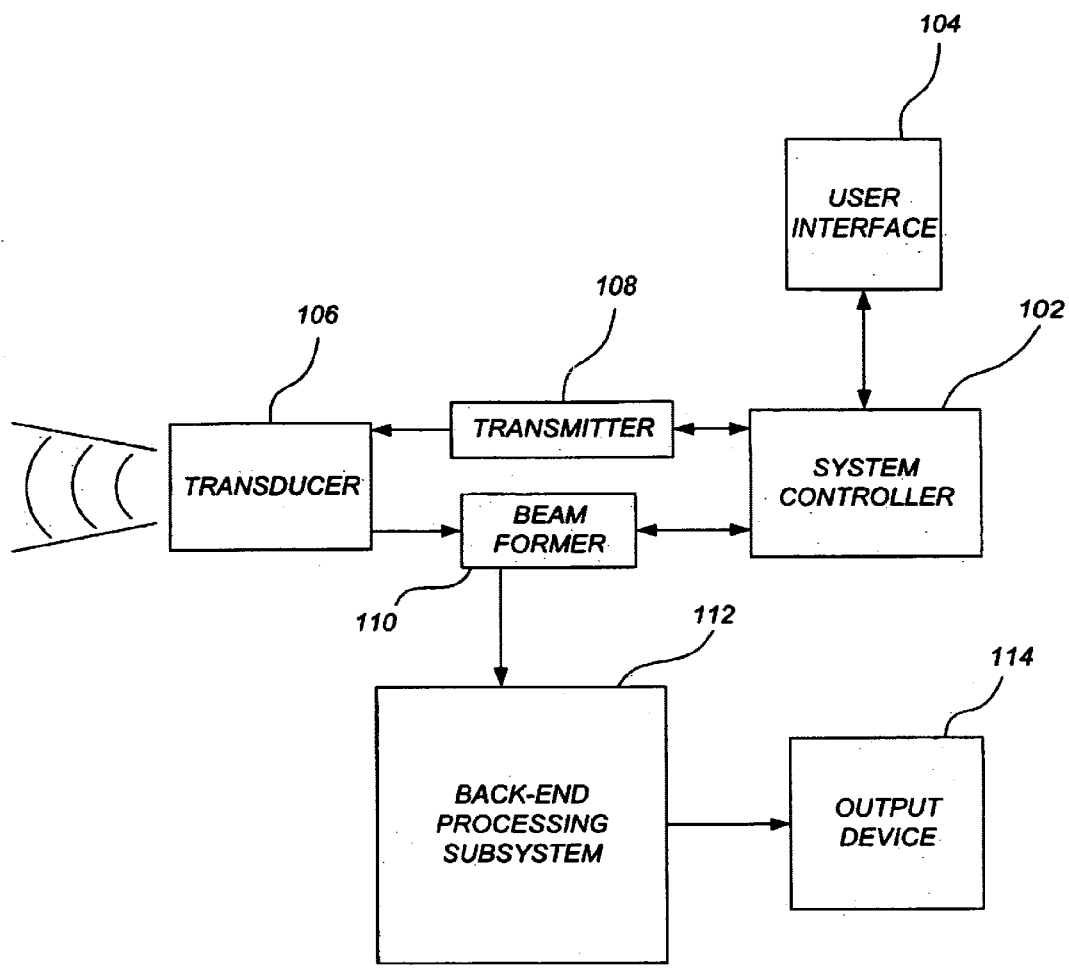
FIG. 1 shows a diagram of one-dimensional probe signals as applied to a target object for determining the acoustic impedance of locations therein.
Figure 2:
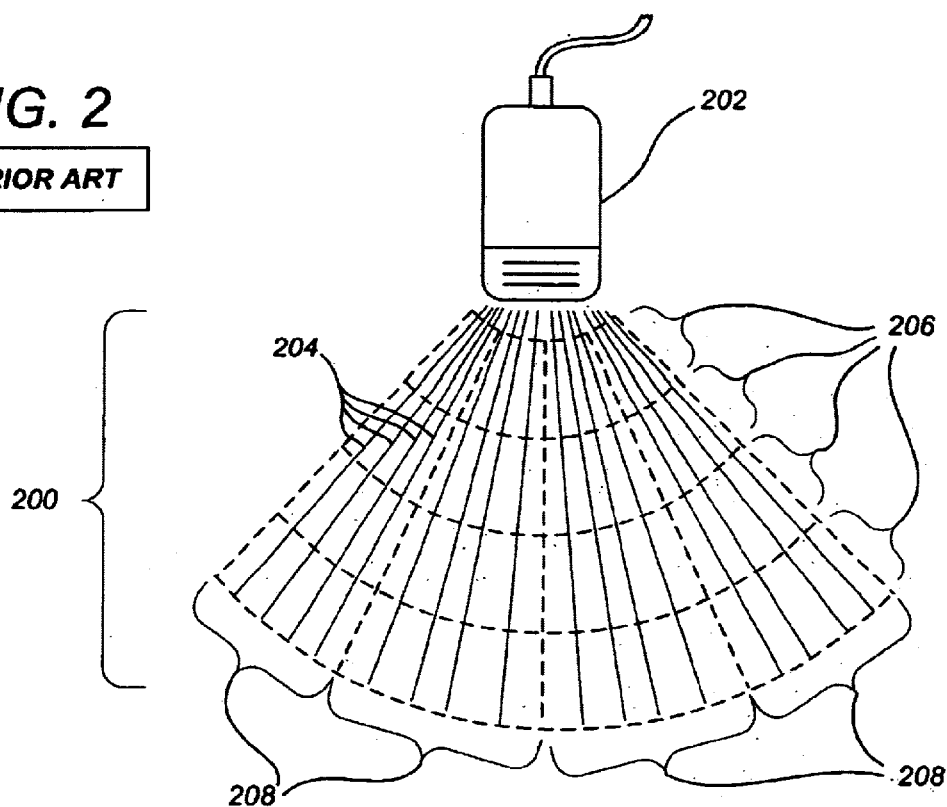
FIG. 2 shows a diagram of an ultrasound frame corresponding to a curved probe.
Figure 3:
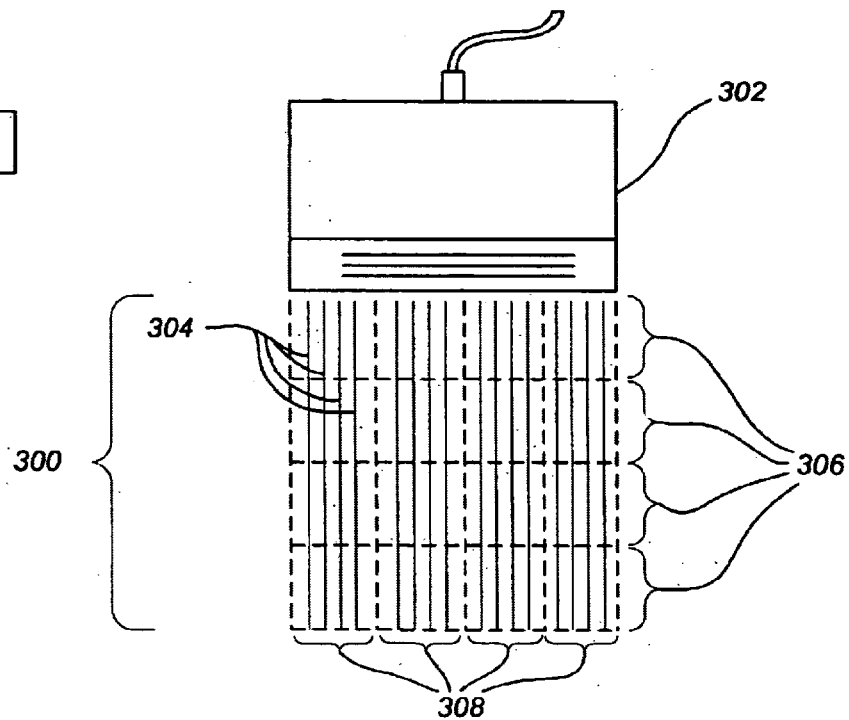
FIG. 3 shows a diagram of an ultrasound frame corresponding to a flat head probe.

Host computer 412 is coupled to a LAN (not shown) for allowing communications with other computer in the same medical facility or with any computer over the Internet as disclosed in application Ser. No. 09/224,635, supra. Host computer 412 also comprises a scan converter for converting image data samples, which generally correspond to digital samples from non-rectangular grids such as those of FIG. 2, into pixelized format for display on a computer monitor. Host computer 412 is also coupled to a user interface 414 using known methods for receiving user commands and displaying processed image data. Non-limiting examples of a user interface 414 that may be used in accordance with the preferred embodiments are shown in Zagzebski, "Essentials of Ultrasound Physics," supra.

Figure 5:
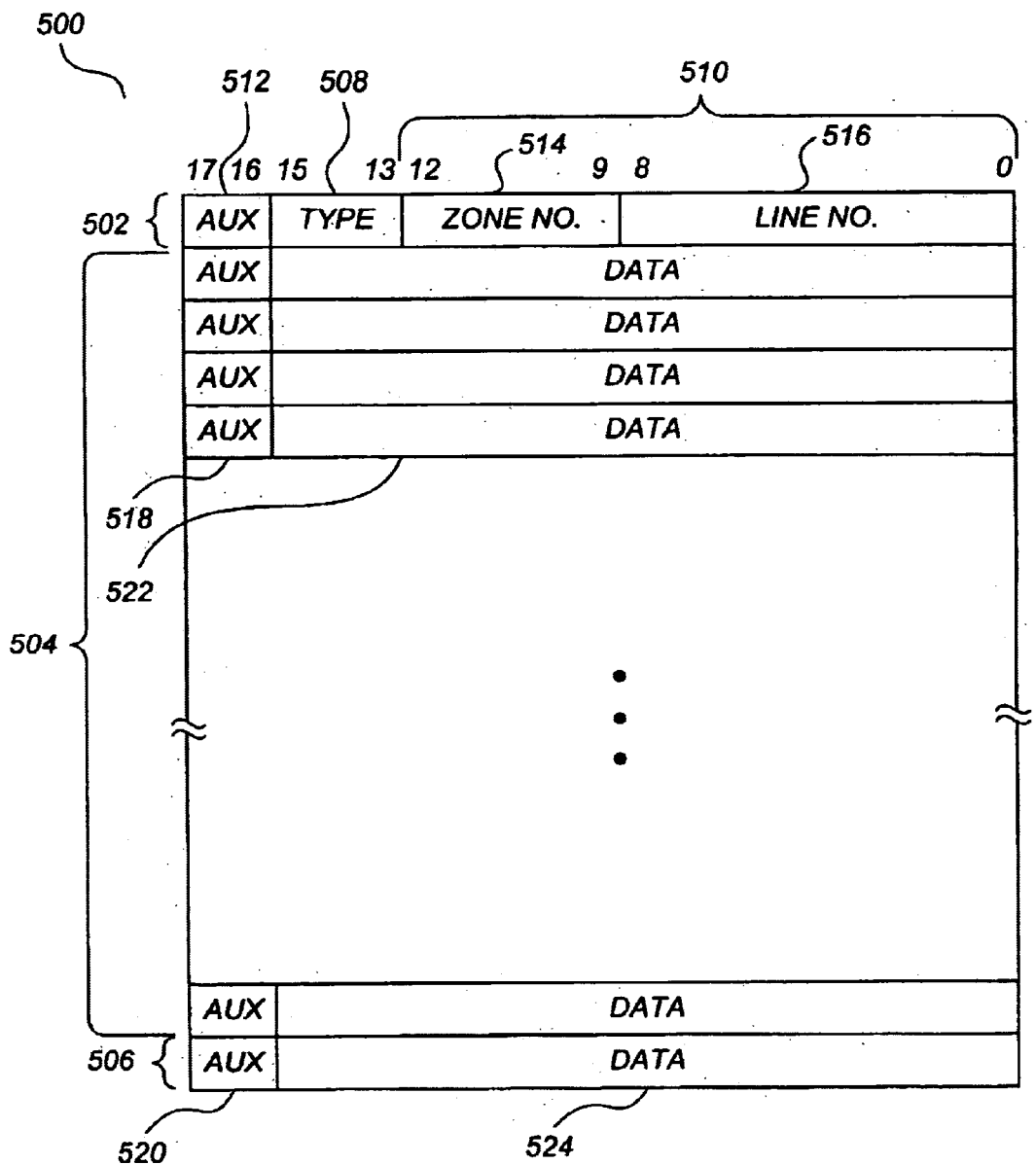
FIG. 5 shows a diagram of an ultrasound information packet in accordance with a preferred embodiment.

FIG. 5 shows a diagram of an exemplary ultrasound information packet 500 formed by demodulator/packetizer 406 and transmitted to digital processing system 408 in accordance with a preferred embodiment. Ultrasound information packet 500 comprises a header 502, a payload 504, and an end sequence 506. Header 502 comprises a type field 508, a location information field 510, and an auxiliary field 512. Location information field 510 comprises a zone number field 514 and a line number field 516. In the example of FIG. 5, type field 508 is a multiple-bit field that identifies the ultrasound imaging mode associated with the ultrasound information packet 500. For example, type field 508 may be a three-bit field that is assigned the binary value 001 for B-mode, the binary value 010 for Doppler-mode, the binary value 100 for M-mode, and the binary value 111 for color mode. Zone number field 514 corresponds to the zone in the ultrasound frame to which the information in ultrasound information packet 500 corresponds for B-mode, Doppler mode, or M-mode imaging, or to an ensemble count for color mode as will be described further infra. Line number field 516 contains the line in the ultrasound frame to which the information in ultrasound information packet 500 corresponds. It is to be appreciated that while the location information field 510 of FIG. 5 comprises zone and line information, it is within the scope of the preferred embodiments for any of a variety of indices to identify location in the ultrasound frame, including index types not commonly used in systems today but for which future utility may arise (e.g., polar coordinates).

Auxiliary field 512 is an optional field that, in a preferred embodiment, may be used by the digital signal processing subsystem 408 to distinguish the header 502 from other entries in the ultrasound information packet 500. For example, in the embodiment of FIG. 5 the auxiliary field 512 within header 502 may be set to binary 01 (START OF PACKET), whereas auxiliary fields 518 within payload entries 504 may be set to binary 00 (VALID PACKET DATA). Auxiliary field 520 corresponding to end sequence 506 may be set to binary 11 (FRAME SWITCH) when the ultrasound information packet 500 corresponds to the final line of an ultrasound frame, and set to binary 00 (VALID PACKET DATA) otherwise. As described further infra, the value of auxiliary field 520 may be used by hardware within the digital signal processing subsystem 408 to detect the end of a frame. In this manner, low-cost hardware dedicated to detecting just the bits corresponding to auxiliary fields 514, 518, and 520 may be used in within digital signal processing subsystem 408 to separate incoming ultrasound information packets from each other and to separate successive ultrasound frames. However, it is also within the scope of the preferred embodiments to omit auxiliary fields 514, 518, and 520, or to otherwise use the bit fields for image data, while using other methods to separate incoming ultrasound information packets from each other and to separate successive ultrasound frames.

As shown in FIG. 5, payload 504 comprises a plurality of payload entries 522 in addition to the auxiliary fields 518. Each payload entry 522 comprises all or part of a digital sample from an ultrasound frame location identified in location information field 510. As an example, for B-mode and M-mode imaging, each of the 16-bit payload entries 520 represents a 16-bit sample value, with the first 8 bits corresponding to an amplitude metric and the second 8 bits corresponding to a phase metric. End sequence 506 comprises a final 16-bit data point 524 similar to the payload entries 522 in addition to the auxiliary field 520. Advantageously, for B-mode, Doppler mode, and M-Mode, the structure of ultrasound information packet 500 is adaptable for a carrying different numbers of digital samples, the number of samples depending on the number of zones along a given line.

Figure 6:
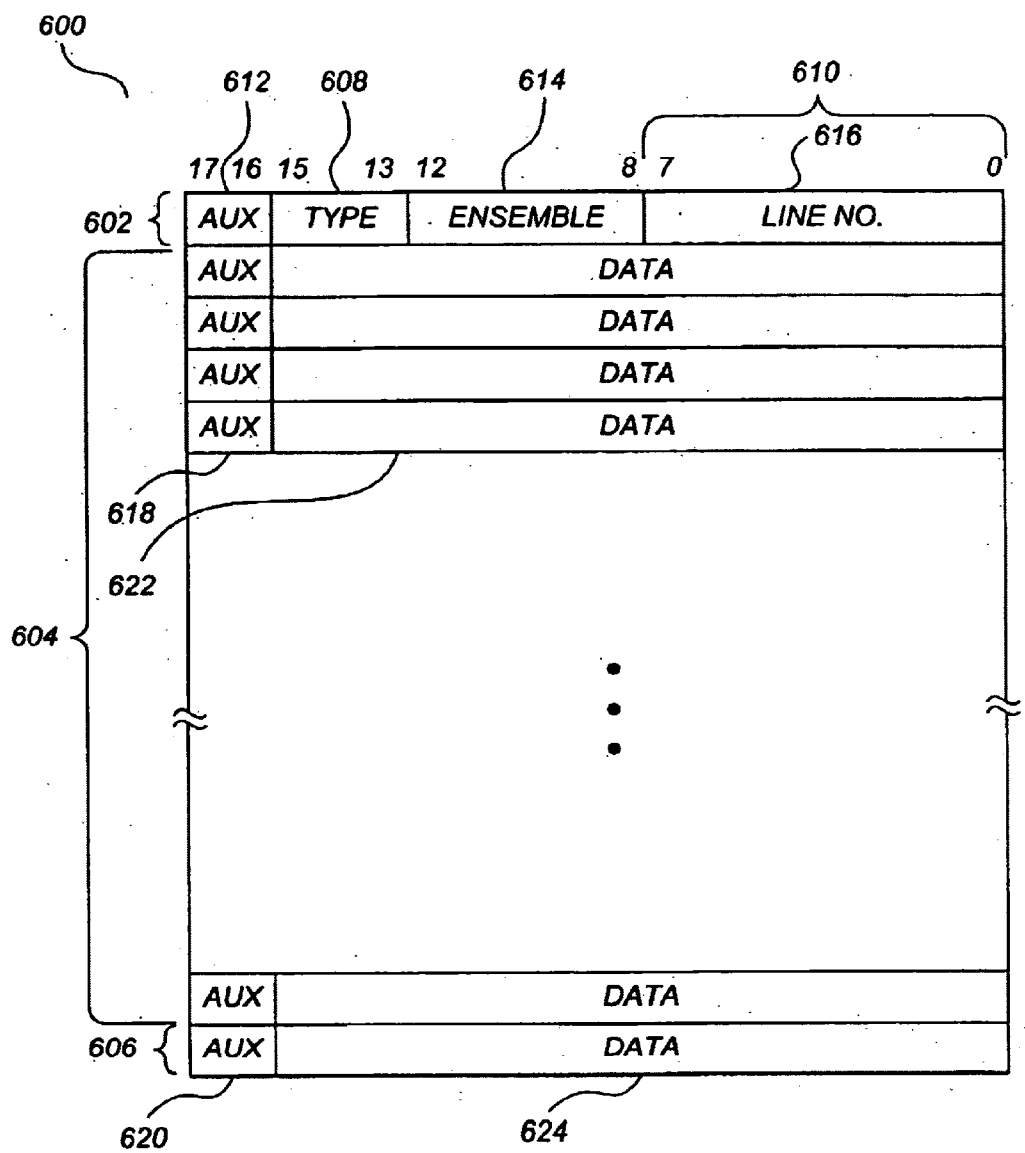
FIG. 6 shows a diagram of a color mode ultrasound information packet in accordance with a preferred embodiment.

FIG. 6 shows a diagram of an ultrasound information packet 600 corresponding to color mode imaging. As known in the art, color mode imaging involves a sequence or ensemble of pulses transmitted down a single line at successive intervals, so that motion of target elements can be detected. When the color mode ultrasound information is packetized in accordance with the preferred embodiments, an ensemble of ultrasound information packets corresponding to the same line at distinct times is generated. Each ultrasound information packet is assigned an ensemble number representing its respective time position in the ensemble. The amount of data for a color mode frame is therefore much larger than for the other ultrasound imaging modes, and resolution is reduced accordingly for a given line to accommodate an acceptable frame rate. In a preferred embodiment, the ultrasound frame in color mode consists of a single zone, whereby each ultrasound information packet no longer requires a zone number field. The zone number information in the zone number field is instead replaced by the ensemble count of the ultrasound information packet. Each line in the color ultrasound frame has a reduced number of digital samples as compared to B-mode or M-mode imaging. For example, whereas a B-mode or M-mode ultrasound frame may comprise up to 1024 digital samples per line, a color ultrasound frame may only comprise 256 digital samples.

As shown in FIG. 6, ultrasound information packet 600 comprises a header 602, a payload 604, and an end sequence 606. Header 602 comprises a type field 608, a location information field 610, an auxiliary field 612, and an ensemble number field 614. Type field 608 is set to binary 111 for color mode. Location information field 610 comprises a line number field 616. Although a zone number field is not necessary for the embodiment of FIG. 6 because there is only a single zone per line, it is nevertheless within the scope of the preferred embodiments that additional location information be present in location information field 610. Ensemble number field 612, shown in the example of FIG. 6 as a 5-bit field, corresponds to the ensemble number of the ultrasound information packet. Accordingly, in a color mode ultrasound information processing system corresponding to the embodiment of FIG. 6, there may be up to 32 pulses sent down the same line at successive time intervals, for determining target motion along that line. Auxiliary field 612 of header 602, as well as auxiliary field 616 in payload 604 and auxiliary field 620 of end sequence 606, are similar in purpose to auxiliary fields 512, 518, and 520 of FIG. 5, although the implementation of auxiliary field 620 is modified as described infra.

Payload 604 comprises a plurality of entries 622 in addition to the auxiliary fields 612. Because color mode imaging requires higher dynamic range readings for each digital sample, each of the 16-bit payload entries 622 comprises half of the information of a digital sample, either a 16-bit amplitude metric ("I") or a 16-bit phase metric ("Q"). In particular, for adjacent successive digital samples along a given line indexed by positions n, n+1, n+2, etc., the data in payload 604 is arranged $I_n, Q_n, I_{n+1}, Q_{n+1}, I_{n+2}, Q_{n+2}$, etc. End sequence 606 comprises a final 16-bit data point 624 set equal to $Q_m$, where m is the index of the last digital sample along the line in the color mode image frame. In a manner similar to auxiliary fields 512 and 518 of FIG. 5, the auxiliary field 612 for header 602 may be set to binary 01 (START OF PACKET), while each auxiliary field 618 for payload 604 may be set to binary 00 (VALID PACKET DATA).

Because it is desirable to use the same hardware in digital signal processing subsystem 408 for color mode imaging, B-mode imaging, and other modes, it has been found that a cost effective solution is to segregate color mode ultrasound frames into subframes. This allows for the use of smaller and less expensive input buffers within digital signal processing subsystem 408, input buffers that are capable of containing entire B-mode image frames but which are too small to contain entire color mode image frames. In accordance with a preferred embodiment, ultrasound information packet 600 is adapted to accommodate subframes by allowing auxiliary field 620 in end sequence 606 to be set to binary 10 (INPUT FRAME SWITCH) when the ultrasound information packet 600 corresponds to the final line of a color mode ultrasound subframe, set to binary 11 (FRAME SWITCH) when the ultrasound information packet 600 corresponds to the final line of an overall color mode ultrasound frame, and set to 00 (VALID PACKET DATA) otherwise.

By way of nonlimiting example, an ultrasound frame may be segregated into two subframes, a left subframe and a right subframe, for color mode imaging. For a given frame, the left subframe is processed first and auxiliary field 620 is set to 00 (VALID PACKET DATA) for all packets until the last packet of the left subframe, when it is set to 10 (INPUT FRAME SWITCH). The right subframe is then processed and auxiliary field 620 is set to 00 (VALID PACKET DATA) for all packets until the last packet of the right subframe when it is set to 11 (FRAME SWITCH). Advantageously, this ultrasound information packet structure allows for hardware within digital signal processing subsystem 408, as described infra, to allow for partial loading of output buffers as successive subframes are input and processed, and to only allow a completed frame to be output after the last subframe of that frame is processed. In this way, overall system cost is kept low because the same hardware in digital signal processing subsystem 408 that is used for B-mode imaging can be used for color mode imaging and other modes, while real-time processing system speed is maintained through the use of a pipelined architecture.

Figure 7:
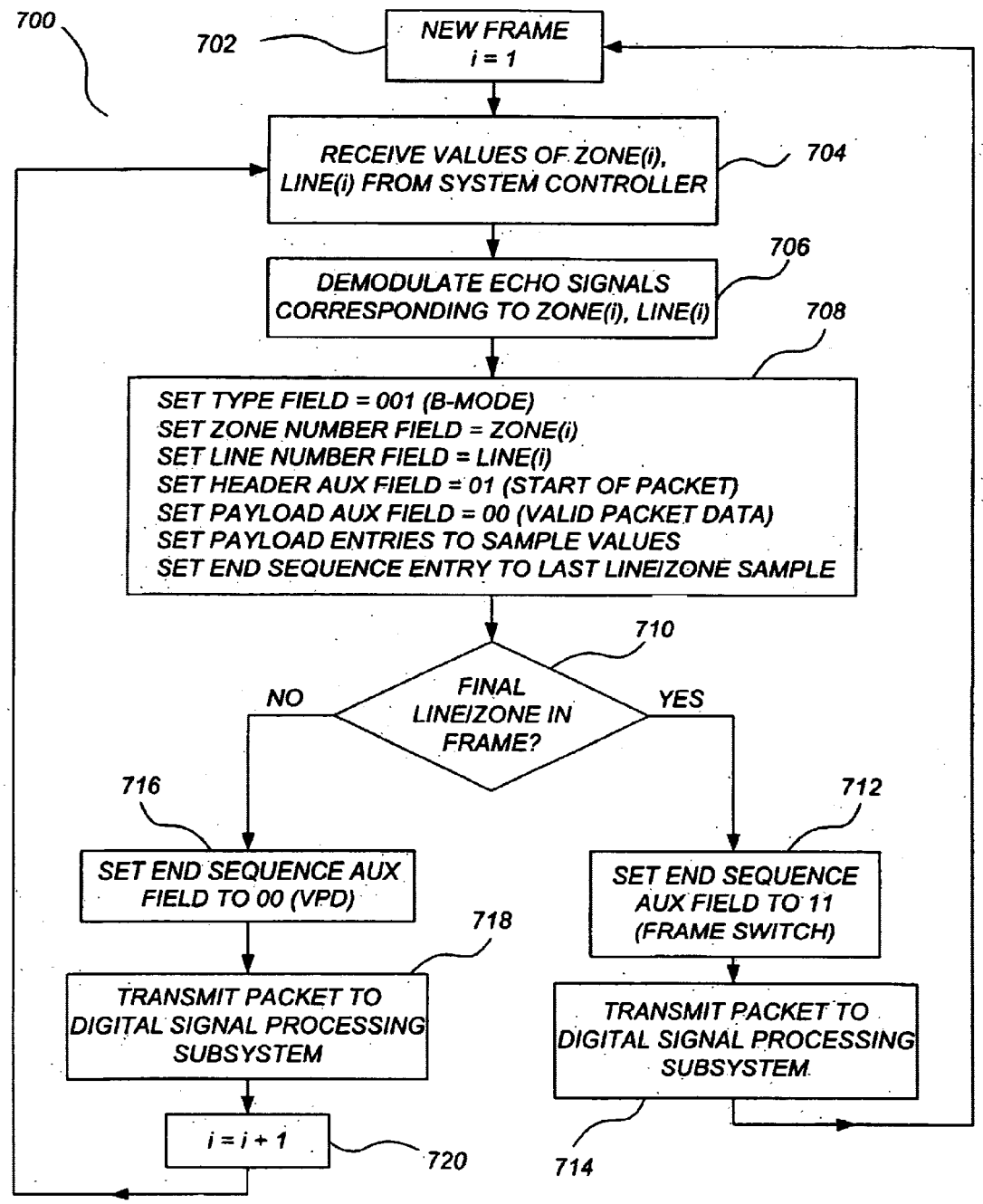
FIG. 7 shows steps for forming an ultrasound information packet in accordance with a preferred embodiment.

FIG. 7 shows steps 700 carried out by front end transmit/receive beamformer 404 and demodulator/packetizer 406 for forming ultrasound information packets in accordance with a preferred embodiment. At step 702, which represents the beginning of a frame, a counter variable "i" is initialized. It is to be understood that counter variable i is used in the present disclosure to identify successive ultrasound information packets and not necessarily to limit the design of elements used to create ultrasound information packets in accordance with a preferred embodiment. At step 704, demodulator/packetizer 406 and front end transmit/receive beamformer 404 receive the values of a zone and a line to be scanned, represented herein by zone(i), and line(i). The values of zone(i) and line (i) are generated by a scan sequencer within system controller 410 and transmitted over the modified ISA bus 420.

Importantly, the values of zone(i) and line(i) may occur in any order including a random order. As known in the art, it is desirable in ultrasound systems not to present physically adjacent pulses in a time sequential order because of interference echoes that may occur from the physically adjacent pulses. Rather, it has been found that a random sequence of line(i) produces better results. In accordance with a preferred embodiment, real time processing is accommodated despite the fact the line data is received in random order. As described further infra, real time processing is permitted through the packetization of the ultrasound scan signals into ultrasound information packets, a routing of the packets to multiple digital signal processors according to a routing table in a manner similar to that performed by Internet routers, and the placement of the routed packets into ping-pong buffer memory banks according to an intrabuffer address also provided by the routing table.

For purposes of better describing the preferred embodiments, the term sector is used herein to identify a plurality of adjacent lines in an ultrasound frame. For example, each of the four different regions identified as elements 208 in FIG. 2 supra, may be identified as a sector of the ultrasound frame 200. In a preferred embodiment, lines from the same sector are routed to the same digital signal processor within digital signal processing subsystem 408, as will be more fully described infra. Advantageously, the demodulator/packetizer 406 is not required to identify the sector associated with a given line line(i). Rather, association of lines to digital signal processors occurs directly by means of a routing table within the digital signal processing subsystem 408, as will be more fully described infra.

At step 706, at a time substantially near when the values of zone(i) and line(i) are received by front end transmit/receive beamformer 404 from system controller 410, front end transmit/receive beam former 404 also receives the values of zone(i) and line (i), and causes an electronically steered ultrasound signal to be transmitted from transducer 402 into the body of the patient at locations corresponding to zone(i) and line (i). Using methods known in the art, echo signals are received and demodulated into digital sample values.

At step 708, using the information of zone(i), line (i), the digital samples, and known mode and other timing information received over modified ISA bus 420, demodulator/packetizer 406 forms and populates an ultrasound information packet 500 as follows. In the example of B-mode imaging, type field 508 is set to 001. It is to be understood that the use of 001 to represent B-mode is for explanatory purposes only, and any of a variety of numbering or tagging schemes may be used to differentiate the different types of ultrasound modes. Also at step 708, zone number field 514 is set to the value of zone(i). The auxiliary field 512 corresponding to header 502 is set to 01 to indicate start of packet. After the header fields are properly populated, the payload field 504 is populated by setting the auxiliary fields of 504 to 00 to represent valid packet data. The payload entries 518 are set to sample values received and demodulated from front end transmit receive beam former 404. Finally, end sequence 506 is formed by setting the end sequence entry 522 equal to last sample value of the line/zone region in question, and by populating the auxiliary field of end sequence 506 as herein described.

Auxiliary field 524 of end sequence 506 serves the purpose of providing a signal to the input buffers of the digital signal processors on digital signal processing subsystem 408 (to be described further infra). This signal identifies whether the ultrasound information packet 500 corresponds to the last packet of an ultrasound frame, or whether there are still future packets to process for that frame. At step 710, it is determined whether or not the present packet represents the final line/zone packet in the frame. This step may be carried out through the receipt of signaling information from modified ISA bus 420 carrying information from a scan sequencer within system controller 410. If the ultrasound information packet 500 is the final line/zone in the ultrasound frame, then step 712 is performed. At step 712, the end sequence auxiliary field 524 is set to 11 (FRAME SWITCH) to represent the need for the input buffers to switch ping-pong memory banks. Following step 712, at step 714, the completed ultrasound information packet is transmitted to the digital signal processing subsystem 408.

However, if it is determined at step 710 that the ultrasound information packet 500 is not the last line/zone packet in the ultrasound frame, then end sequence 524 is set to 00 (VALID PACKET DATA) at step 716 to represent that the next ultrasound information packet will be associated with that same frame. At step 718 the completed packet is sent to digital signal processing subsystem 408. At step 720, the counter variable "i" is incremented, and the process is repeated.

Importantly, the above steps only correspond to simpler modes of ultrasound imaging such as B-mode, Doppler mode, and M-mode. For color ultrasound imaging modes, a modified process is used to populate the ultrasound information packets.

Figure 8:
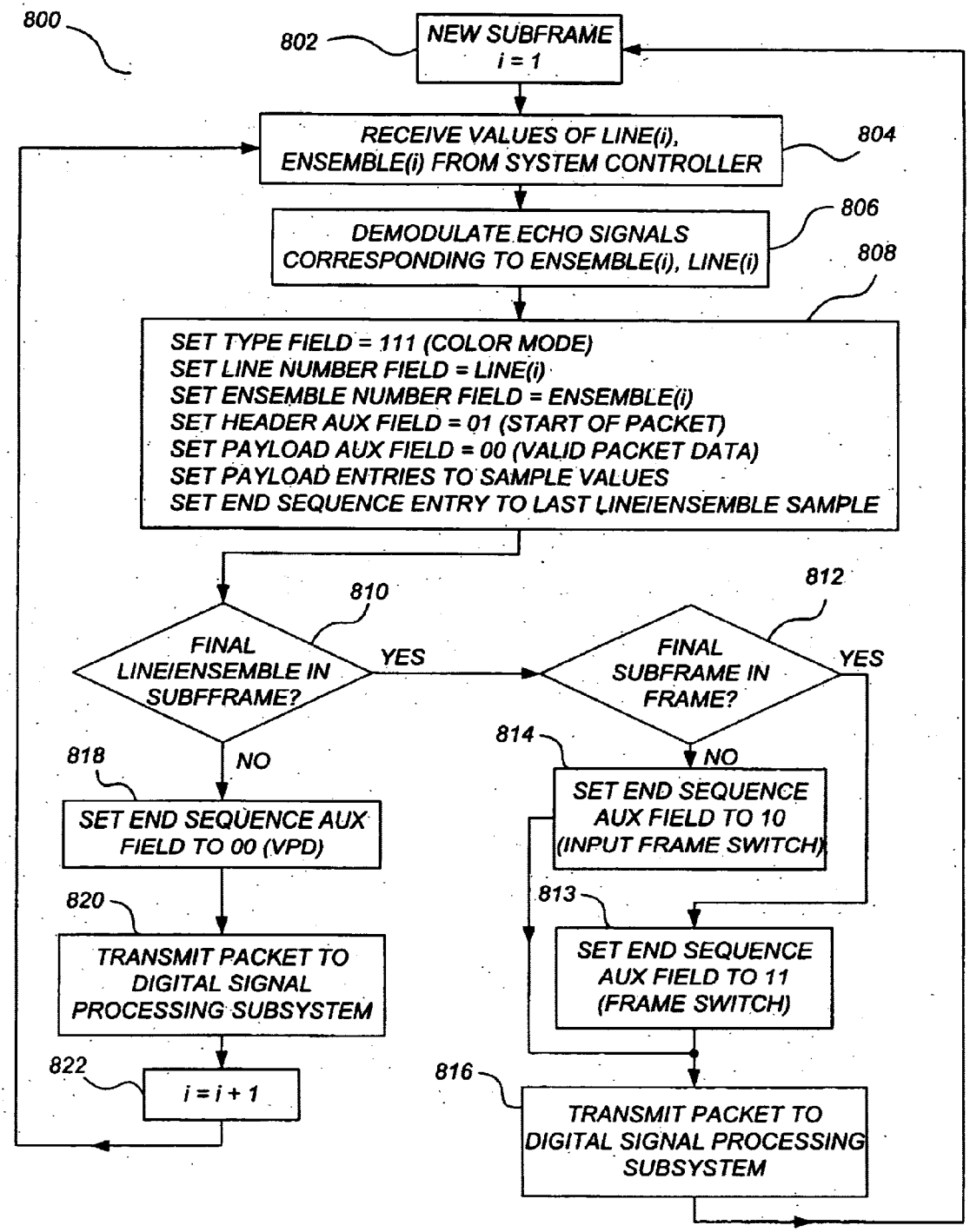
FIG. 8 shows steps for forming a color mode ultrasound information packet in accordance with a preferred embodiment.

FIG. 8 shows steps 800 for constructing a color mode ultrasound information packet in accordance with a preferred environment. A counter variable i is initialized at step 802 in a manner similar to step 702 in FIG. 7. As disclosed supra, for color mode imaging applications, there is a single zone on any given line of an ultrasound frame. The color mode ultrasound information packet 600 of FIG. 6 differs from the non-color mode ultrasound information packet 500 of FIG. 5 in that the ensemble number of a color mode pulse is recorded in the header instead of the zone number. In this manner, a time index may be known by the digital signal processors to allow movement to be measured at a given location.

At step 804, an ensemble number ensemble(i) and a line number line(i) are received from system controller 410. Advantageously, not only may the sequence line(i) occur in a random order, but also, in accordance with a preferred embodiment, the ensemble pulses associated with a given line do not need to be transmitted successively in time. The architecture disclosed herein accommodates for ultrasound pulse sequences in which not all ensemble members along a given line need to be transmitted sequentially by transducer 402. Thus, for example, the sequence of pulses may occur in the following order: . . . , line 47, ensemble count 9; line 122, ensemble count 2; line 47, ensemble count 10; line 8, ensemble count 1; line 122, ensemble count 3; line 47, ensemble count 11, and so on. This allows for added flexibility, wherein line(i) may be a random variable function, and wherein the routing and intrabuffer addressing is performed such that the ultrasound information is sent to the appropriate processor as well as to the appropriate location within the input buffer of that processor such that the DMA accesses from the digital signal processor are taken from ordered buffer data.

At step 806, the ultrasound pulses are demodulated and echo signals corresponding to ensemble(i) and line(i) are formed into digital samples. At step 808 the fields of ultrasound information packet 600 are populated, starting with the type field 612 of header 602 being set to 111 to represent color mode. The line number field 616 is set to line(i), the ensemble number field 614 is set to ensemble(i), and the header auxiliary field 612 is set to 01 t(START OF PACKET). The auxiliary fields 618 of payload 604 are set to 00 (VALID PACKET DATA), and payload entries 622 are set to the sample values as described supra with respect to FIG. 6. The auxiliary field 620 of end sequence 606 is then populated as herein described.

As discussed supra with respect to color mode imaging, it is necessary to differentiate between whether an ultrasound information packet represents the final line/ensemble within an entire frame, the final line/ensemble within just a subframe of that frame, or neither. At step 810, it is determined whether ultrasound information packet 600 is the final line/ensemble packet within a subframe. As with B-mode imaging and other modes, this is also determined through signals received over ISA bus 420 from system controller 410. If the ultrasound information packet 600 is indeed the final line/ensemble packet in the subframe, then at step 812 it is determined whether that subframe is the final subframe of the overall color ultrasound image frame. If yes, then end sequence auxiliary field 620 is sent to 11 (FRAME SWITCH) at step 813 to indicate a the need for an entire frame switch at the input buffers of the digital signal processors, as will be described infra. If it was not the final subframe in the frame, then at step 814 the end sequence auxiliary field 620 is set to 10 (INPUT FRAME SWITCH) to indicate to the input buffers that they may continue to be populated with information from the next ultrasound information in the current ping pong buffer bank. Subsequent to either step 814 or step 812, at step 816 the color ultrasound information packet 600 is transmitted to digital signal processing subsystem 408.

If the ultrasound information packet 600 is not at the end of a subframe as determined at step 810, then at step 818 end field sequence auxiliary field 620 is set to 00 (VALID PACKET DATA), the ultrasound information packet 600 is sent to the digital signal processing subsystem 408 at step. 820, and at step 822 the counter i is incremented and the process is repeated.

Figure 9:
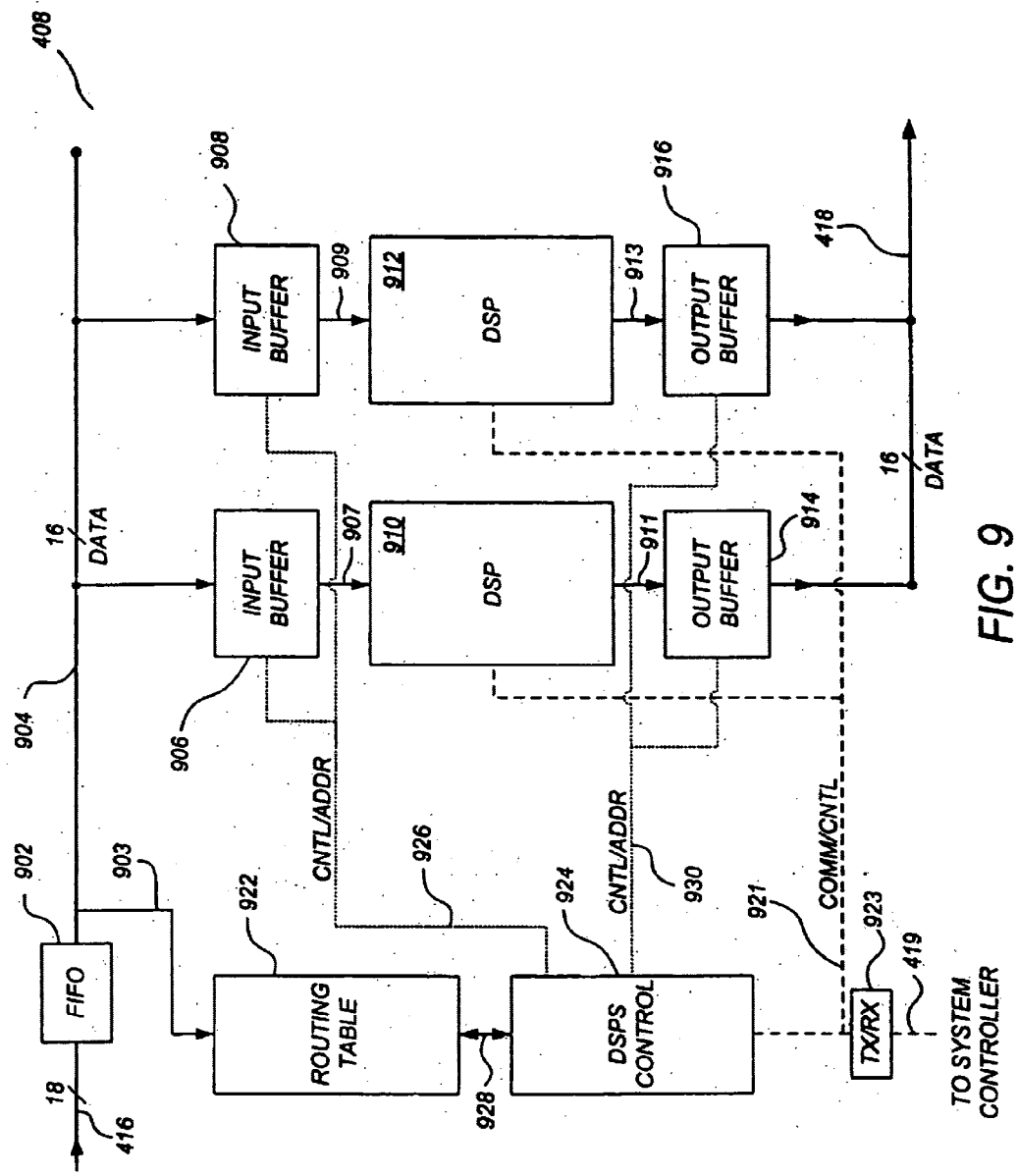
FIG. 9 shows a block diagram of a two-processor implementation of a digital signal processing subsystem of the ultrasound information processing system of FIG. 4.

FIG. 9 shows a block diagram of a digital signal processing subsystem 408 in accordance with a preferred embodiment. Digital signal processing subsystem 408 comprises a FIFO buffer 902 that receives ultrasound information packets from demodulator/packetizer 406 over bus 416. The output of FIFO 902 is coupled to an input data bus 904, which in turn is coupled to input buffers 906 and 908, respectively. The input buffers 906 and 908 are in turn coupled to digital signal processor 910 and digital signal processor 912, respectively, via buses 907 and 909, respectively. Digital signal processors 910 and 912 may comprise any of a variety of a high speed processing chips having signal processing instructions sets. In a preferred embodiment, TMS320C6202 digital signal processors are used, which are available from Texas Instruments, Inc., http://www.ti.com. The setup, configuration, and programming of the TMS320C6202 digital signal processors are described in publicly available Texas Instruments literature document numbers SPRU190B and SPRU189C (March 1998), the contents of which are incorporated by reference into the present disclosure, and other publicly available documents.

Digital signal processors 910 and 912 are in turn coupled to output buffers 914 and 916, respectively, via buses 911 and 913, respectively, and the output buffers 914 and 916 in turn are coupled to output bus 418. The data present on output bus 418 represents ultrasound image data that has been processed according to any of a variety of two dimensional image processing algorithms that may be programmed into and performed by the digital signal processors 910 and 912, respectively.

Digital signal processing subsystem 408 further comprises a routing table 922 and a digital signal processing subsystem control block 924 for providing routing and control functions. Using routing data loaded into routing table 922, digital signal processing subsystem control block 924 properly distributes incoming ultrasound information packets to the appropriate digital signal processors and to the appropriate intrabuffer addresses of the input buffers corresponding to those digital signal processors. Routing table 922 is coupled to input data bus 904 via lines 903 and is adapted to receive only the header and auxiliary field information from each ultrasound information packet. Based on the header information, the appropriate input buffer 906 or 908 is activated to receive that ultrasound information packet, the signaling and destination intrabuffer address being provided by means of input control bus 926. Routing table 922 is coupled to digital signal processing subsystem control block 924 through one or more data connections represented by element 928 in FIG. 9. It is to be appreciated that the routing table and control functions may be integrated together into a common RAM configuration with outputs of the RAM representing the control signals over input control bus 926 and an output control bus 930 for controlling output buffers 914 and 916. More general, however, is the configuration shown in FIG. 9 in which routing table information can be used by control circuitry to activate and deactivate a plurality of input buffers or output buffers as necessary.

The input buffers 906 and 908, which are detailed infra, each comprise a ping-pong buffer that holds two complete image frames, wherein one image frame may be DMA-accessed by the associated digital signal processor while the other is being populated by ultrasound information packets as routed by routing table 922. Thus, in operation, when an ultrasound information packet is being transmitted over input data bus 904, the routing table 922 has already derived the appropriate destination based on the header information in that ultrasound information packet, and has activated the destination input buffer (or input buffers). When the next ultrasound information packet arrives, the routing table likewise sends it to the appropriate input buffer, and so on until the final packet of an ultrasound information frame indicates to input buffers 906 and 908 to switch sides, and ultrasound information packets from the next frame then are used to populate the opposite side of the input buffers.

In accordance with a preferred embodiment digital signal processing subsystem control block 924 and digital signal processors 910 and 912 are coupled to system controller 410 through a communications/control bus 921. Communications/control bus 921 is coupled to control link 419 through a transceiver 923, the control link leading to the system controller 410. It is to be appreciated that details of communication/control bus 921 and its communicative coupling to system controller 410 would be achievable by a person skilled in the art in view of the present disclosure. Control link 419 carries information needed by digital signal processing subsystem control block 924 and digital signal processors 910 and 912 in real time or non-real-time as required. For example, loading of the digital signal processors 910 and 912 with the desired two dimensional image processing algorithms to be used is usually performed in non-real time, as well as the loading of routing table data into routing table 922. However, during a detected malfunction of one of the processors during image processing operations, it is within the scope of the preferred embodiments to perform in real time the loading of the program of the malfunctioning processor into a spare processor (not shown) and to modify the routing table to redirect ultrasound information packets from the malfunctioning processor to the spare processor.

Generally speaking, digital signal processing subsystem 408 in accordance with a preferred embodiment contains several advantages through the use of the routing table 922, the ping-pong input and output buffers 906, 908, 914, and 916, and the dual bus configuration represented by input data bus 904 and output data bus 418. In particular, while the configuration of FIG. 9 is a two-digital signal processor configuration, the digital signal processing subsystem 408 is readily expandable by adding additional digital signal processors, and their associated input and output ping-pong buffers. Likewise, a spare digital signal processor and its associated input and output ping-pong buffers may be coupled between the input data bus 904 and the output data bus 418 for providing system redundancy and increased reliability. Because of the parallel nature of the input data bus 904, the output data bus 418, and the control/address lines 926 and 930, these digital signal processor may be simply and flexibly connected to the system by adding additional hardware boards to a parallel system backplane containing these data buses. When new hardware is added, as in an upgrade to the digital signal processor 408, the routing table 922 is updated to include more destination processors for incoming ultrasound information packets. The ability to add and take away processing segments or processing boards allows for ready system flexibility, a flexible cost and marketing structure, and ready upgradability. For example, if an ultrasound system purchaser only wants a basic system they can order just a single digital signal processor configuration, but as their image processing needs increase they can purchase additional signal processor boards and readily install them in the system. Generally speaking, as more digital signal processor boards are added, each digital signal processor chip is responsible for less of a part of the ultrasound image frame, and therefore can accomplish more complicated digital signal processing algorithms in real time.

Figure 10:
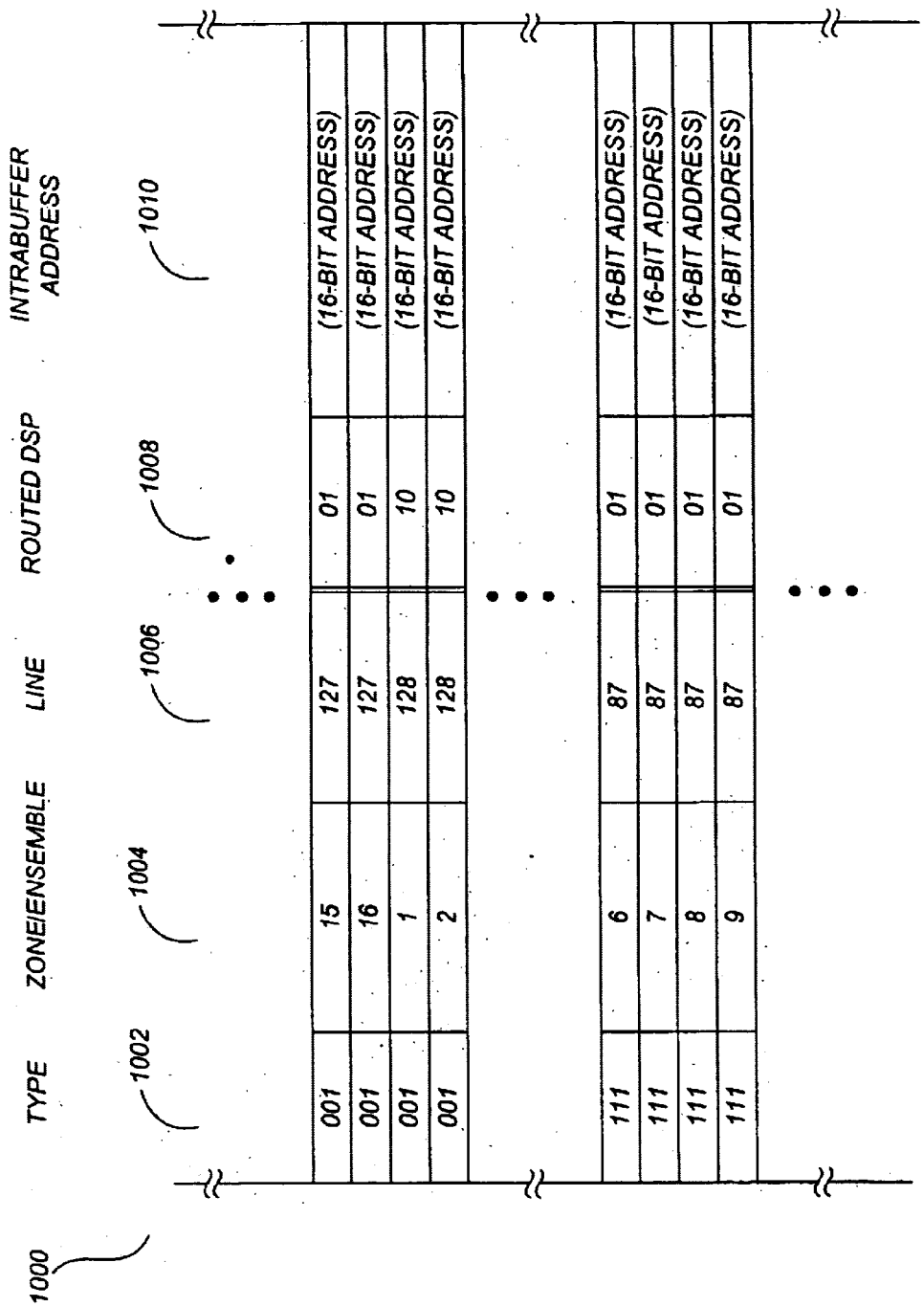
FIG. 10 shows sections of routing data that may be loaded into a routing table of the digital signal processing subsystem of FIG. 9.

FIG. 10 shows a portion of routing data 1000 that may be loaded into routing table 922 in accordance with a preferred embodiment. It is to be appreciated that only a simplified example is demonstrated in FIG. 10 so as not to cloud the features and advantages of the preferred embodiments. It is to be understood that a person skilled in the art would be able to determine appropriate routing data in view of the present disclosure and the desired mathematical algorithm. Routing data 1000 comprises type information 1002, zone or ensemble information 1004, and line information 1006. These values correspond to header information of arriving ultrasound information packets. Routing data 1000 further comprises routed DSP information 1008 and intrabuffer address information 1010 such that, responsive to the header information in an arriving ultrasound information packet, that packet is routed to the desired destination digital signal processor(s) and to the appropriate address within the input buffer(s) associated with the desired destination digital signal processor(s).

In the upper portion of routing data 1000 in FIG. 10, an example for B-mode routing data shown for routing ultrasound information packets originated near a boundary of an ultrasound frame sector. In the desired algorithm, all lines in the ultrasound frame less than line 127 are considered to be in a first sector of the ultrasound frame and to be processed by a first digital signal processor, and all lines in the ultrasound greater than or equal to line 128 are considered to be in a second sector of the ultrasound frame and are to be processed by a second digital signal processor. Accordingly, in the routed DSP field 1008, for line 127 there is a value of to 01 to represent the first digital signal processor 910, and for line 128 there is an output of 10 to represent the second digital signal processor 912. The intrabuffer address information 1008 provides an intrabuffer destination address for the ultrasound information packet payload data, such that after the input buffer memory bank is loaded, the image data therein is stored in proper order and not in the random time order of the ultrasound information packets.

In the lower portion of routing data 1000 in FIG. 10, are exemplary elements of color mode routing data as indicated by the type information being set to 111. As shown therein, the ultrasound information packets are routed and assigned intrabuffer addresses according to line number and ensemble number. For clarity of disclosure, there is no sector boundary present in the routing data of the lower portion of FIG. 10, and all ultrasound information packets are simply forwarded to the second digital signal processor 912. Along a sector boundary there would be differences in routed DSP field 1008 to indicate different destination digital signal processors for the different sectors.

Figure 11:
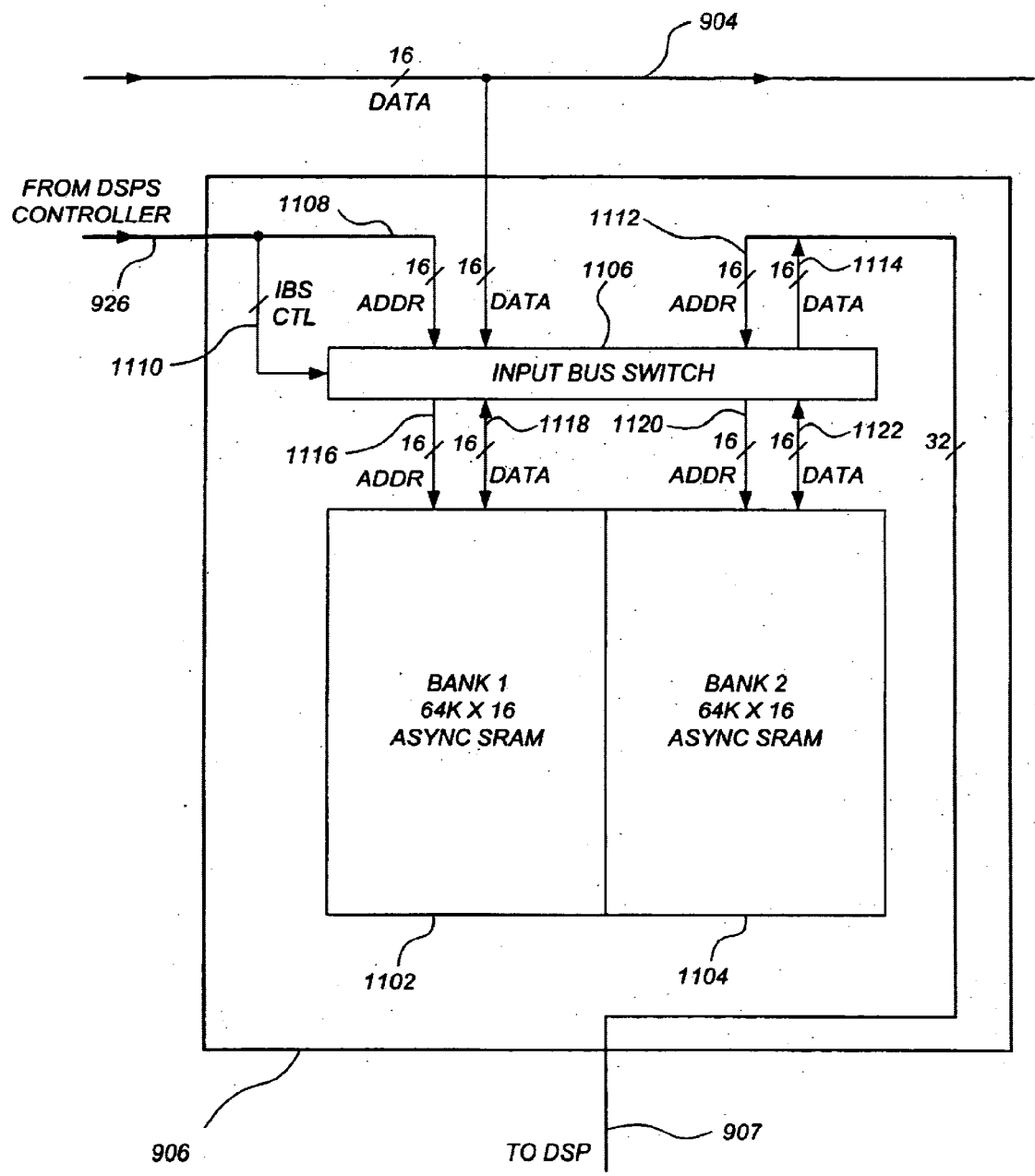
FIG. 11 shows a block diagram of an input buffer of the digital signal processing subsystem of FIG. 9.

FIG. 11 shows a block diagram of input buffer 906 in accordance with a preferred embodiment. Input buffer 906 comprises a first memory bank 1102 of asynchronous static RAM that is dimensioned, for example, to 64K×16, and a second memory bank of asynchronous static RAM 1104, that is identical to the first bank. For B-mode processing, each bank of 64K×16 is sufficient to hold a 256×256 sector of 16-bit digital samples. The memory size may be increased to hold more data as the power of digital signal processor 910 is increased. Input buffer 906 further comprises a bus switch 1106 for directing the traffic of ultrasound image data into and out of the memory banks 1102 and 1104. Bus switch 1106 is coupled to input data bus 904 for receiving the ultrasound information packets data and is coupled to digital signal processing subsystem controller 924 by control leads 926, the control leads 926 further comprising a 16-bit address lead 1108 and a multi-bit input bus control line 1110. Bus switch 1106 is also coupled to bus 907 leading to digital signal processor 910, the 32-bit bus 907 comprising a 16-bit address bus 1112 and a 16-bit data bus 1104. Bus switch 1106 is coupled to the first memory bank 1102 through a 16-bit address bus 1116 and a 16-bit data bus 1118, and is coupled to second memory bank 1104 through a 16-bit address bus 1120 and a 16-bit data bus 1122.

Input buffer 906 is adapted and configured to run in a ping-pong buffer fashion using the architecture shown in FIG. 11. Ultrasound information packets from the same ultrasound frame or subframe are stored in one of the memory banks 1102 or 1104 during a first period and, during a second period for a subsequent frame, the ultrasound information packets are stored in the other memory bank.

In a B-mode imaging operation, for example, during a first period when a first frame is being loaded, bus switch 1106 directly connects address bus 1108 to address bus 1106 and input data bus 904 to data bus 1118 responsive to settings of IBS control bus 1110, wherein incoming ultrasound information packet data is written directly to the first memory bank 1102 at the intrabuffer address being provided over control bus 926. At the same time, bus switch 1106 directly connects address buses 1112 and 1120, and directly connects data buses 1114 and 1112, whereby digital signal processor 910 performs DMA memory access operations on the image data being stored in the second memory bank 1104.

Subsequently, at a second time when a second frame is being loaded, bus switch 1106 directly connects address bus 1108 to address bus 1120 and data bus 904 to data bus 1122 such that the ultrasound information packet data is directly loaded into the second memory bank 1104 at the intrabuffer address being provided over control bus 926. At the same time, bus switch 1106 directly connects address line 1112 to address line 1116 and data lines 1114 to data line 1118, such that digital signal processor 910 performs DMA memory access operations on the image data being stored in the second memory bank 1104. Subsequently, during a third time when a third ultrasound frame is being loaded, the operation is again reversed, such that image data is being loaded into the first memory bank 1102 while image data is being DMA-accessed from the second memory bank, and so on. Using a ping-pong buffer in this manner, digital signal processor 910 has a consistently populated data frame upon which to perform DMA access, and will not have to wait for loading of ultrasound information data, thereby enhancing real time processing capability. Additionally, because the image data is already in proper order, the digital signal processor 910 is not required to spend CPU cycles rearranging the data before starting two-dimensional image processing operations on the data.

Figure 12:
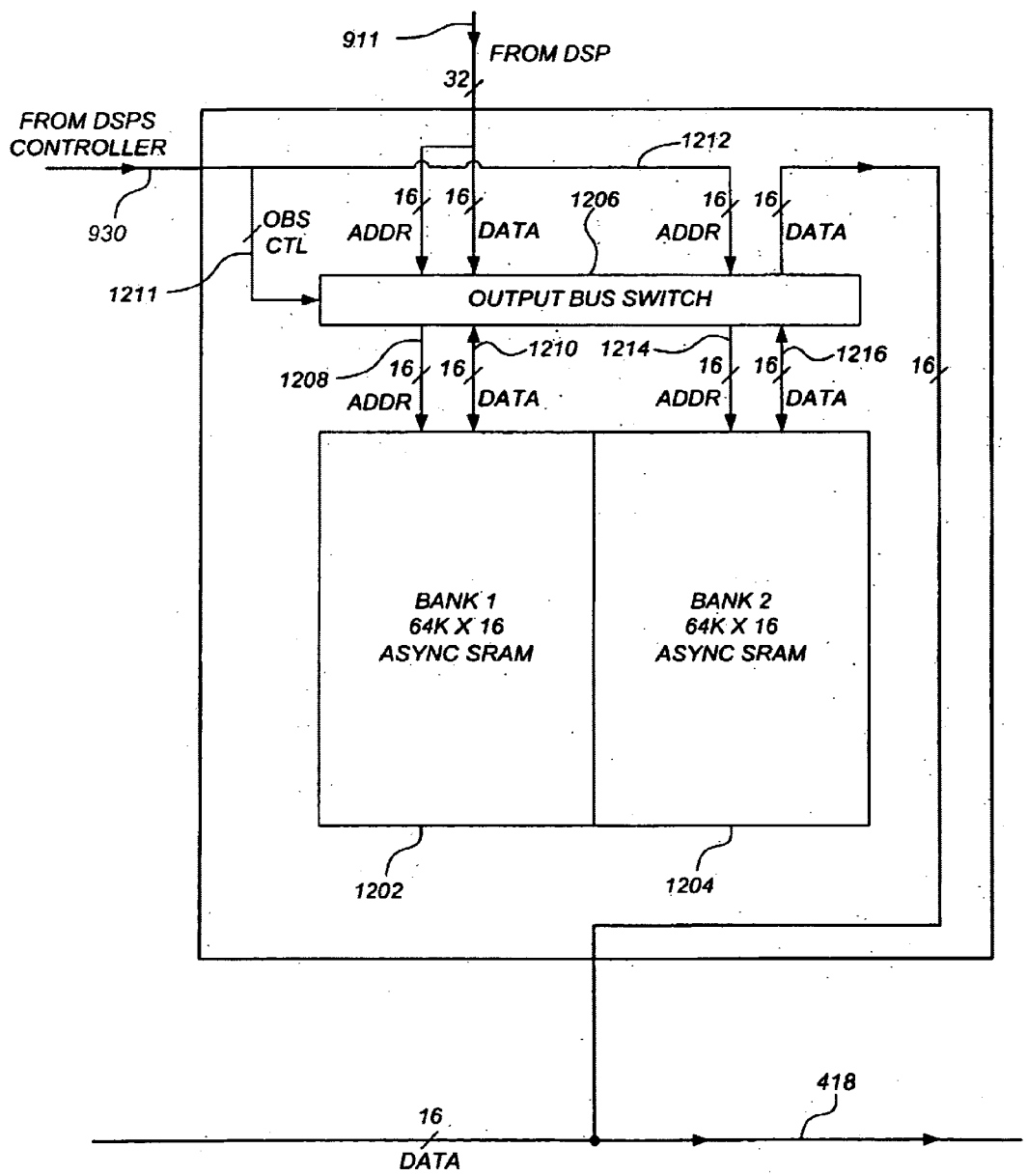
FIG. 12 shows a block diagram of an output buffer of the digital signal processing subsystem of FIG. 9.

FIG. 12 shows a block diagram of output buffer 914 in accordance with a preferred embodiment. Similar to input buffer 906, output buffer 914 comprises a first memory bank of asynchronous SRAM 1202 and an identical second memory bank of asynchronous. SRAM 1204 having the same dimensions as the memory banks 1102 and 1104 of input buffer 906. First and second memory banks 1202 and 1204 operate in a ping-pong fashion in conjunction with output bus switch 1206. In accordance with a preferred embodiment, digital signal processing subsystem controller 924 serially instructs the output buffers 914 and 916 to output data bus 918 such that ordered, processed ultrasound information is transmitted to parallel to IEEE 1394 converter 920.

During operation, during a first frame period, output bus switch 1206 directly connects the address and data lines from bus 911 to address and data lines 1208 and 1210, respectively, such that processed data from digital signal processor 910 is loaded directly into the first memory bank 1202. At the same time, or during a subinterval thereof as needed to completely unload the second memory bank 1204 onto output data bus 918, output bus switch 1206 directly connects the address leads 1212 of control bus 930 to the address bus 1214, and connects the data leads of output bus 418 directly to a data bus 1216. During this time interval, digital signal processing subsystem controller 924 provides a sequence of addresses such that data from bank two is serially unloaded onto output bus 418. In a preferred embodiment, the speed of the unloading operation is fast enough such that all output buffers in the digital signal processing subsystem 408 are capable of unloading their data onto the output bus 418.

During a second frame period, as dictated by the signals on OBS control lead 1211, output bus switch directly connects the address and data leads from bus 911 to the address and data leads 1214 and 1216, respectively, such that digital signal processor 910 directly loads processed ultrasound image data into the second memory bank 1204. At the same time, output bus switch 1206 directly connects address leads 1212 from digital signal processing subsystem controller 924 to address leads 1208, and couples the output data leads 418 to the data leads 1210. Accordingly, during the second frame period when data is being written to the second memory bank 1204 from the digital signal processor 910, data is being unloaded read from the first memory bank 1202 onto the output data bus 418. Subsequently, during a third frame period, the operation is again reversed such that image data is being loaded into the first memory bank 1202 from digital signal processor 910 while image data is unloaded from the second memory bank onto output bus 418, and so on.

Figure 13:
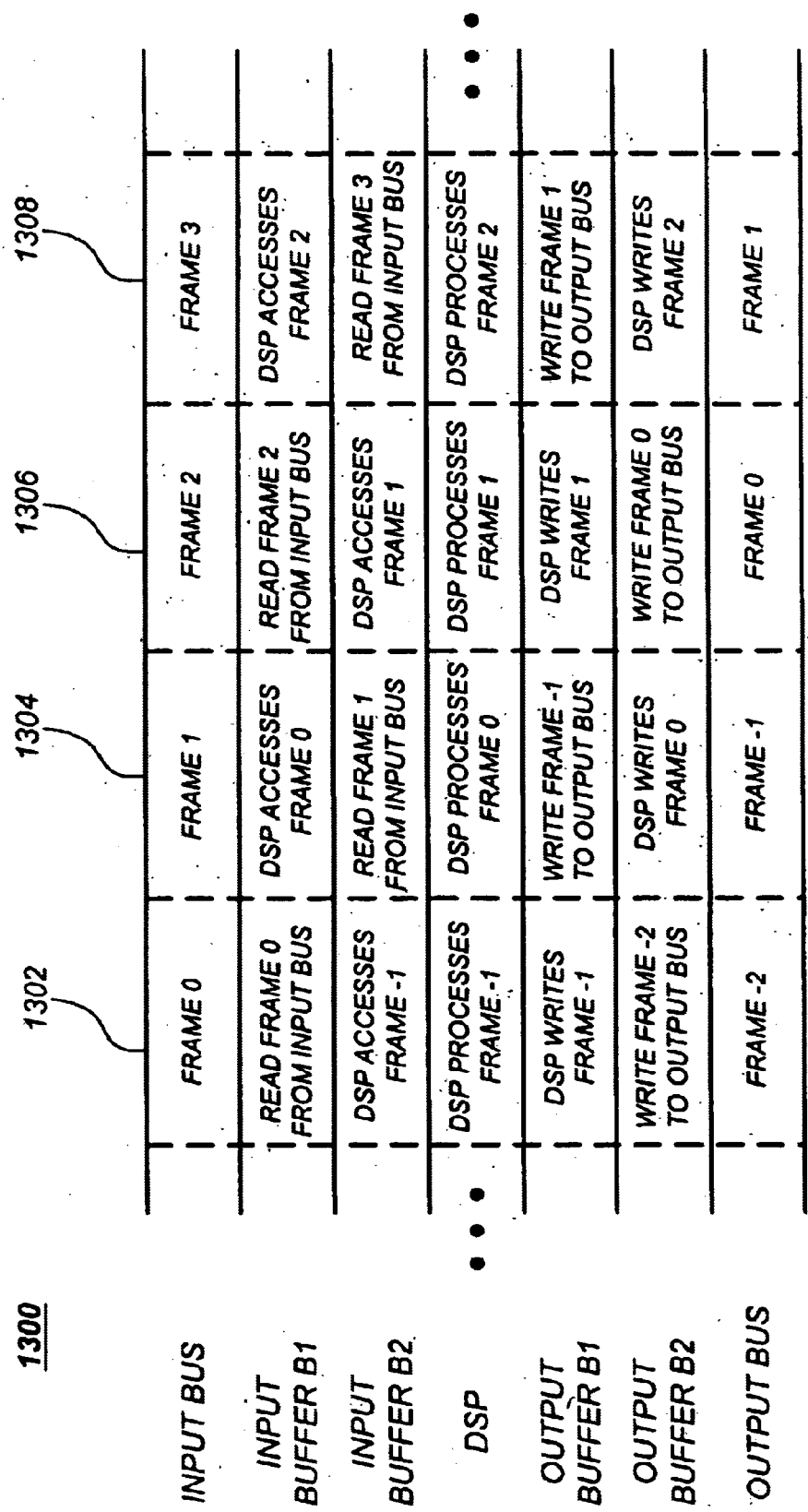
FIG. 13 shows a data processing flow diagram corresponding to a digital signal processor of FIG. 9 and its associated input and output buffers.

FIG. 13 summarizes data flow on digital signal processing subsystem 408 with respect to input buffer 906, digital signal processor 910, and output buffer 914. In accordance with the parallel architecture of the system, each digital signal processor and its associated input and output buffers operate according to the same timing diagram with respect to frame level activities, and differ only in that they process ultrasound information packet from different portions of an ultrasound frame. In this manner, there is a truly distributed processing operation being performed on an ultrasound information frame, and processing speed or complexity may be increased through the addition of additional digital signal processor elements and their associated input and output buffers with minimal changes and configuration to existing hardware. Rather, to add additional processing capability the routing table 922 and the mathematical algorithms loaded into the digital signal processors 910 and 912 would be updated with new information.

As shown in FIG. 13 during a first interval 1302 out of a sample sequence of intervals 1302, 1304, 1306, and 1308, the first memory bank of the input buffer reads "frame 0" while the second memory bank of the input buffer is allowing the digital signal processor chip to access and process data from "frame −1". Importantly, in accordance with a preferred embodiment, digital signal processor 910 processes an entire frame with no frame latency and writes the results from "frame −1" to the first memory bank of the output buffer during the same interval as it reads "frame −1" from the second memory bank of the input buffer. This is provided in a preferred embodiment by the Texas Instruments TMS320C6202, which has an internal configuration in which 4 smaller batches of image data (16K×16) may be accessed and processed in an internal pipeline within the processor. While the processor is processing a previous batch of sampled data, the DMA channel can directly access the input buffer to move in a new batch of data into one of the smaller internal bank memories.

In the meantime, during the first interval 1302, the second memory bank of the output buffer contains results from "frame −2" which is serially written to the output bus. Accordingly, while "frame −2" is being written to the output bus, "frame 0" is being read in the input bus.

During a second interval 1304, the input buffer banks and output buffer banks perform reverse functions as compared to the first interval 1302, wherein the first memory bank of the input buffer is allowing the digital signal processor DMA-access to its image data while the second memory bank of the input buffer is loading "frame 1" from of the input bus. Likewise, the first memory bank of the output buffer is writing the results of "frame −1" to the output bus while second memory bank of the output buffer is receiving the results of processed "frame 0: from the digital signal processor. It is to be appreciated that the general timing diagram of FIG. 13 is also followed when there are additional digital signal processor chips on board. Advantageously, the addition of additional digital signal processor processing power does not change the overall ping-pong operation of the existing input buffers, output buffers, and digital signal processors on the existing board.

Figure 14:
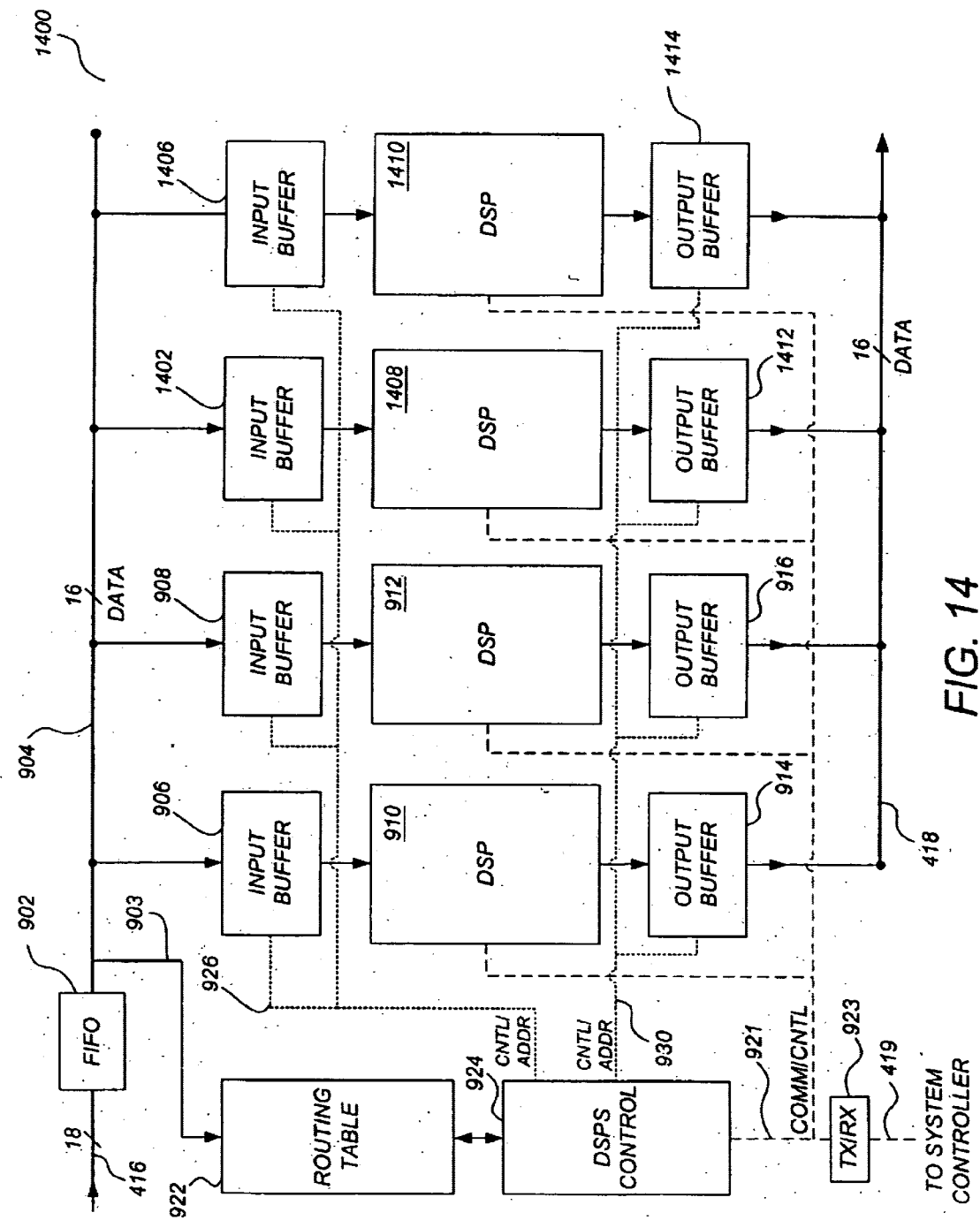
FIG. 14 shows a block diagram of a four-processor implementation of a digital signal processing subsystem of the ultrasound information processing system of FIG. 4.

FIG. 14 shows a four-processor digital signal processing subsystem 1400 in accordance with a preferred embodiment.

The digital signal processing subsystem 1400 is similar to the digital signal processing subsystem 408 of FIG. 9 except that additional digital signal processors and their associated input and output buffers have been added. As shown in FIG. 14, a digital signal processing subsystem in accordance with a preferred embodiment is easily upgraded through the addition of digital signal processors and their associated input buffers to the input and output data bus pairs, as well as to the control/address lines from the routing table and the digital signal processor control blocks.

As shown in FIG. 14, digital signal processing subsystem 1400 comprises elements similar to the two-digital signal processor subsystem 900 of FIG. 9. However, digital signal processing subsystem 1400 also comprises additional input buffers 1402 and 1406 that have been coupled to input buffer control/address bus 926 and input data bus 904. Additionally, digital signal processors 1408 and 1410 have been added and coupled to input buffers 1402 and 1406, respectively, and to communication/control bus 923 for coupling to system controller 410 and digital signal processing subsystem control block 924. Finally, output buffers 1412 and 1414 have been added between digital signal processors 1408 and 1410 and the output bus 418, as well as to output, buffer control/address bus 930. Advantageously, a system in accordance with preferred embodiments is easily upgraded simply through the addition of additional hardware board coupled to a common back plane. Also, according to a preferred embodiment, if a digital signal processor chip malfunctions the routing table 922 may be automatically reprogrammed to operate at, a slower rate and with fewer active digital signal processors in an on-the-fly manner.

Figure 15:
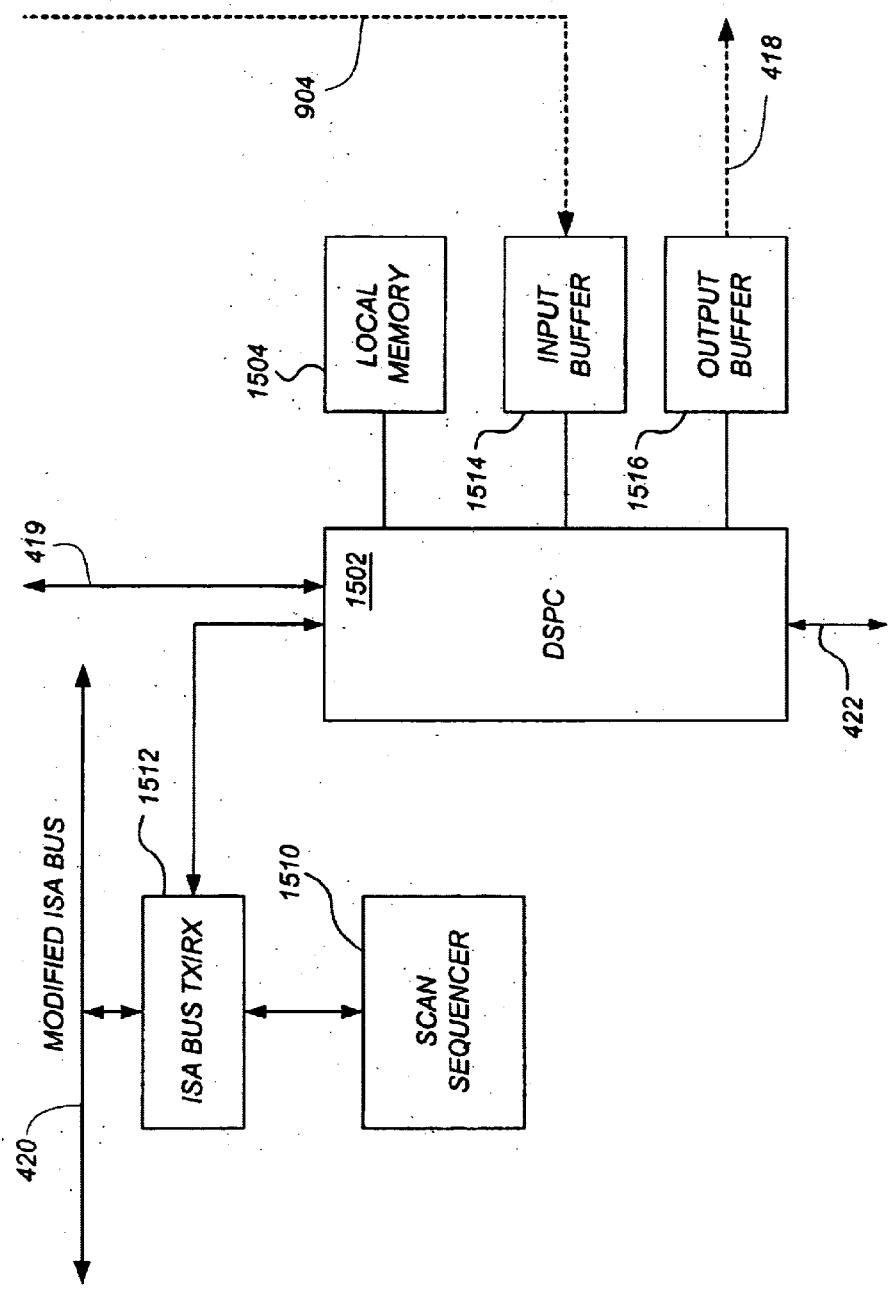
FIG. 15 shows a block diagram of a system controller the ultrasound information processing system of FIG. 4.

FIG. 15 shows a block diagram of a system controller 410 in accordance with a preferred embodiment. System controller 410 comprises an embedded controller 1502 which, in a preferred embodiment, is similar to the digital signal processor chips 910 and 912. Advantageously, in accordance with a preferred embodiment, the ultrasound information processing system 400 may be optionally adapted such that no digital signal processing subsystem 408 is present at all, and all processing is be performed solely by use of the embedded controller. It is to be appreciated, that while this is a low-cost configuration, there are only limited ultrasound imaging modes that may be used that do not require significant processing, such as M-Mode. In accordance with the preferred embodiments, a customer may begin by only buying an ultrasound information system 400 not equipped with digital signal processing subsystem 408 but may later choose to upgrade by simply purchasing hardware cards containing one or more elements of digital signal processing subsystem 408 and plugging them into a common back plane.

In operation, system controller 410 communicates with digital signal processing subsystem 408 using the link 419 which is coupled to embedded controller 1502. System controller 410 further comprises a scan sequencer 1510 for performing scan sequencing functions as know in the art, the scan sequencer 1510 being coupled to an ISA bus transceiver 1512. ISA bus transceiver 15.12 transmits commands from embedded processor 1502 and scan sequences from scan sequencer 1510 over the modified ISA bus to the transmit/receive beamformer 404 and the demodulator/packetizer 406.

System controller 410 further comprises a local memory 1504 used by embedded controller 1502 in its various administrative functions related to operation of the ultrasound information processing system 400. System controller 410 further comprises an input buffer 1514 and an output buffer 1516 that are similar to input and output buffers 906 and 908 of FIG. 9, respectively, which may be used in the option low-cost implementation in which the embedded controller 1502 performs the substantive image processing operations and a separate digital signal processing subsystem 408 is not included. In such configuration, input buffer 1514 is coupled to input bus 904 and output buffer 1516 is coupled to output bus 418. Among its various administrative functions, embedded controller 1502 performs the functions of code downloading, routing table programming, and malfunction detection and isolation.

Figure 16:
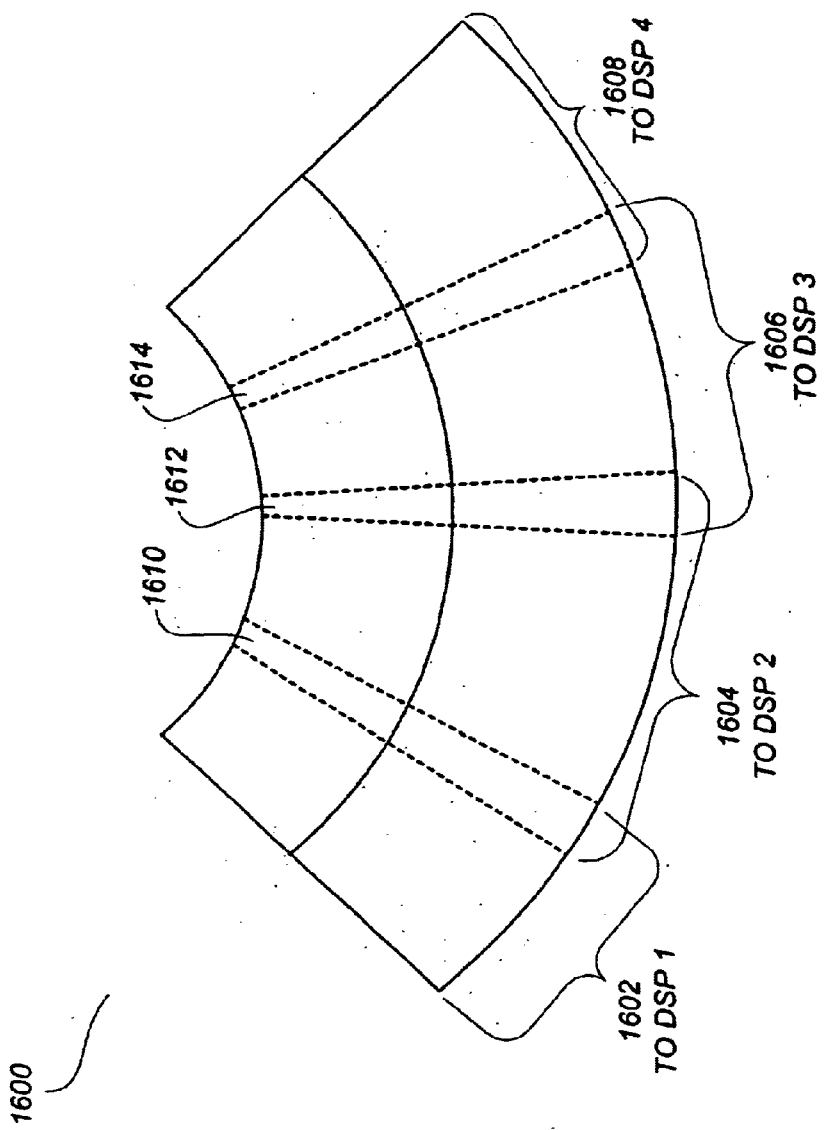
FIG. 16 shows a diagram of an ultrasound frame as subdivided into overlapping sectors.

FIG. 16 shows a diagram of an ultrasound frame 1600 having sectors arranged in accordance with a overlapping zone configuration in accordance with a preferred embodiment. It is often desirable to perform spatial image processing algorithms on adjacent sectors of ultrasound image frames such as those of FIG. 2. However, some spatial signal processing algorithms, such as 3×3 or 5×5 smoothing or gradient operations, for example, may yield adverse results along edge lines because data in adjacent sectors is not available to that processor. Although the TMS320C6202 family of digital signal processors is capable of communication using additional data lines to share edge information with each other, it would be desirable to provide a faster method of processing information such that one portion of ultrasound frame data may be shared among more than one digital signal processor processor.

FIG. 16 shows a plurality of sectors 1602, 1604, 1606, and 1608 which overlap at ultrasound frame regions 1610, 1612, and 1614. In accordance with a preferred embodiment, it is allowed for the sector 1602 to be sent to a first digital signal processor, sector 1604 to be sent to a second digital signal processor, sector 1606 to be sent to a third digital signal processor, and sector 1608 to be sent to a fourth digital signal processor, whereby lines from the region 1610 are sent to both the first and second digital signal processors, lines from the region 1612 are sent to both the second and third digital signal processors, and lines from the region 1614 may be sent to both the third and fourth processors.

FIG. 17 shows a diagram of routing data 1700 that may be programmed into routing table 922 in accordance with a preferred embodiment to allow for the transmittal of overlapping sector regions to more than one digital signal processor chip. Routing data 1700 comprises type information 1702, zone or ensemble information 1704, and line information 1706 similar to the information 1002, 1004, and 1006, respectively, of FIG. 10. However, in a routed DSP field 1708, in a configuration corresponding to four digital signal processor processors, more than digital signal processor indicator is allowed to be set to "1" such that the digital signal processor controller 924 may signal the input buffers of more than one digital signal processor to accept data from that ultrasound information packet. Additionally, in addition to a first intrabuffer address field 1710 for the first target digital signal processor, an additional intrabuffer address field 1712 is included for directing the ultrasound information packet to the correct address within the input buffer corresponding to the second target digital signal processor. As shown in FIG. 17, when a given line of data is only sent to one digital signal processor, the data in field 1712 for the second target digital signal processor is a NULL value as it is not used nor sent to any of the input buffers for addressing purposes. Thus, in accordance with the preferred embodiments, in addition to hardware flexibility to accommodate processing and cost, a configuration is provided in which the ultrasound information processing system 400 may also be updated such that overlapping ultrasound frame sectors is accommodated for better sector edge results.

Figure 18A:
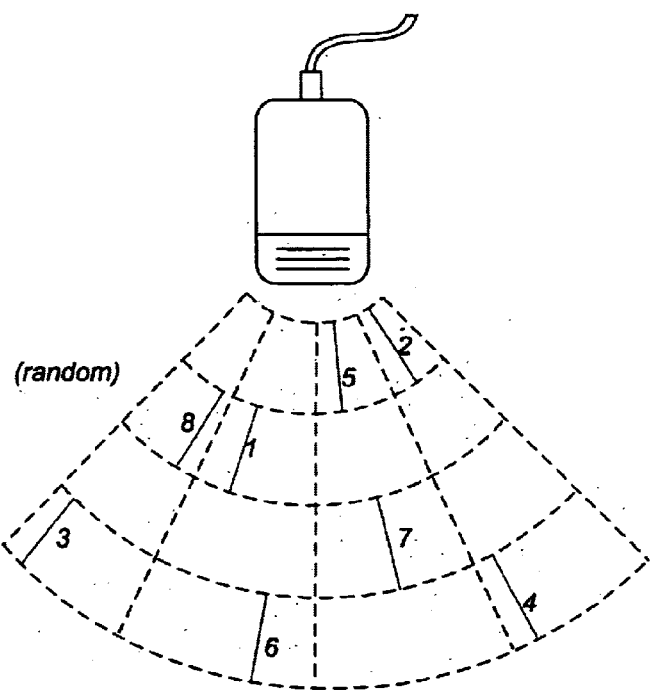
FIG. 18(a) shows a diagram of an ultrasound frame for which scans are taken in random order.
Figure 18B:
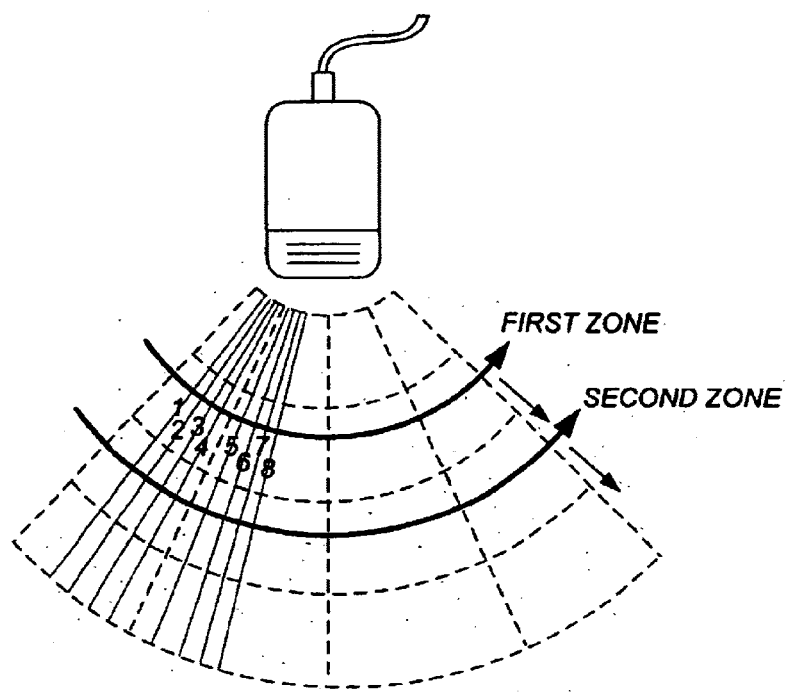
FIG. 18(b) shows a diagram of an ultrasound frame for which scans are taken sequentially by line and then by zone.
Figure 18C:
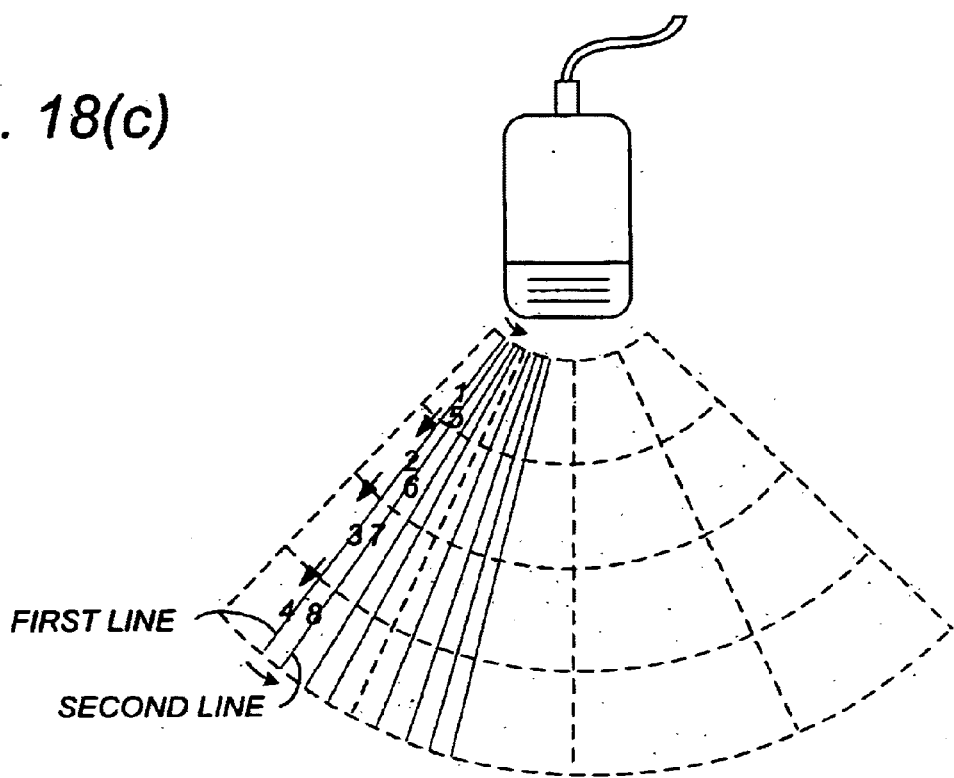
FIG. 18(c) shows a diagram of an ultrasound frame for which scan signals are taken sequentially by zone and then by line.

FIGS. 18(a)–18(c) show diagrams of exemplary sequences of lines and zones (line(i) and zone(i), respectively) that may be generated by scan sequencer 1510 in accordance with a preferred embodiment. FIG. 18(a) shows a diagram of a random scan sequence as described supra with respect to FIG. 7. Although the architecture of the preferred embodiments may advantageously process ultrasound information from randomly arriving lines and zones, it is to be appreciated that ordered line and zone processing may also be achieved in accordance with the preferred embodiments. For example, FIG. 18(b) shows a sequence of lines and zones in which all lines in a first zone are sequentially scanned, followed by all lines in a second zone, and so on. As another example, FIG. 18(c) shows a sequence of lines and zones in which all zones along a, first line are sequentially scanned, followed by all zones along a second line, and so on. Advantageously, the use of a routing table to route incoming packetized ultrasound information to destination input buffers and processors allows for any of a variety of scan sequences to be used, including the above random and ordered sequences and other sequences.

While certain preferred embodiments have been described, these descriptions are merely illustrative and are not intended to limit the scope of the preferred embodiments. For example, although embodiments including two and four digital signal processors were described, within the scope of the preferred embodiments is an ultrasound information processing system having a single processor or having six, eight, or even more digital signal processors. As a further example, within the scope of the preferred embodiments is an ultrasound information processing system that is distributed in time, space, or both, wherein ultrasound information packets are be formed at a first time or location, and then stored until a later time and/or transmitted to a second location (e.g., across town or across the world over the Internet) for the performance of imaging processing operations on the digital samples contained in the ultrasound information packets.

What is claimed is:

1. An apparatus for processing ultrasound data, comprising:

packetizing circuitry for organizing the ultrasound data into ultrasound information packets, said ultrasound information packets comprising location information and corresponding image data;

a plurality of processors for performing image processing operations on said image data a routing table for storing routing data that associates each ultrasound information packet with a subset of said processors according to said location information within that ultrasound information packet;

control circuitry for routing each ultrasound information packet to the subset of processors associated with said ultrasound information packet according to said routing data, an output bus for transferring processed image data from said plurality of processors to an output device;

a distribution bus coupled to said packetizing circuitry for distributing said ultrasound information packets to said processors; and for each processor, an input buffer coupled to said distribution bus, said control circuitry routing said ultrasound information packet to the subset of processors associated with said ultrasound information packet by instructing the input buffers associated with said subset of processors to read from said distribution bus when said ultrasound information packet is present on said distribution bus, each of said input buffers comprising a ping-pong buffer having a first memory bank and a second memory bank, said ping-pong buffer being adapted to load image data into said first memory bank from said distribution bus while the processor associated with said input buffer is readings image data from said second memory bank, said ping-pong buffer being adapted to load image data into said second memory bank from said distribution bus while said processor is reading image data from said first memory bank;

wherein said ultrasound data is derived from transducer outputs associated with an ultrasound frame, said ultrasound frame comprising at least one zone and a plurality of lines, said location information in said ultrasound information packets comprising:

a zone number corresponding to the zone of the ultrasound frame associated with the image data in said ultrasound information packet, said zone being associated with a depth metric in said ultrasound frame with respect to said transducer; and a line number corresponding to the line of the ultrasound frame associated with the image data in said ultrasound information packet, each ultrasound information packet being routed to said subset of processors based on its line number;

wherein said ultrasound frame comprises a plurality of sectors, each sector comprising a plurality of adjacent lines in said ultrasound frame, wherein each processor is associated with a unique sector of said ultrasound frame, whereby each of said ultrasound information packets is routed to a single one of said processors; and wherein said processors are sequentially associated with adjacent sectors of said ultrasound frame, wherein said apparatus further comprises, for each processor, an output buffer coupled to said output bus, and wherein said output buffers sequentially write to said output bus for transfer to said output device.

2. An apparatus for processing ultrasound data, comprising:

packetizing circuitry for organizing the ultrasound data into ultrasound information packets, said ultrasound information packets comprising location information and corresponding image data;

a plurality of processors for performing image processing operations on said image data;

a routing table for storing routing data that associates each ultrasound information packet with a subset of said processors according to said location information within that ultrasound information packet;

control circuitry for routing each ultrasound information packet to the subset of processors associated with said ultrasound information packet according to said routing data;

an output bus for transferring processed image data from said plurality of processors to an output device;

a distribution bus coupled to said packetizing circuitry for distributing said ultrasound information packets to said processors; and for each processor, an input buffer coupled to said distribution bus, said control circuitry routing said ultrasound information packet to the subset of processors associated with said ultrasound information packet by instructing the input buffers associated with said subset of processors to read from said distribution bus when said ultrasound information packet is present on said distribution bus, each of said input buffers comprising a ping-pong buffer having a first memory bank and a second memory bank, said ping-pong buffer being adapted to load image data into said first memory bank from said distribution bus while the processor associated with said input buffer is reading image data from said second memory bank, said ping-pong buffer being adapted to load image data into said second memory bank from said distribution bus while said processor is reading image data from said first memory bank;

wherein said ultrasound data is derived from transducer outputs associated with an ultrasound frame, said ultrasound frame comprising at least one zone and a plurality of lines, said location information in said ultrasound information packets comprising:

a zone number corresponding to the zone of the ultrasound frame associated with the image data in said ultrasound information packet, said zone being associated with a depth metric in said ultrasound frame with respect to said transducer; and a line number corresponding to the line of the ultrasound frame associated with the image data in said ultrasound information packet, each ultrasound information packet being routed to said subset of processors based on its line number;

wherein said apparatus further comprises:

an embedded controller coupled to said control circuitry, to each of said processors, and to said routing table; and a host computer coupled to said embedded controller over a high speed serial link, said embedded controller being adapted and configured to receive image processing programs from said host computer and to download said image processing programs into said processors, said embedded controller being adapted and configured to receive routing data from said host computer and to transfer said routing data to said control circuitry for loading into said routing table; and wherein said embedded controller is capable of detecting a malfunctioning of any of said processors; said apparatus further comprising a spare processor coupled to said distribution bus and said output bus, said embedded controller and said host computer being configured such that upon detection of a malfunctioning of one of said processors, said spare processor is automatically programmed with a copy of a program being run by the malfunctioning processor, and said routing table is automatically modified such that ultrasound information packets initially directed to said malfunctioning processor prior to the malfunction are directed to said spare processor, whereby image processing functions of a malfunctioning processors are automatically redirected to said spare processor for increasing field reliability of said apparatus.

3. An apparatus for processing ultrasound data, comprising:

packetizing circuitry for organizing the ultrasound data into ultrasound information packets, said ultrasound information packets comprising location information and corresponding image data;

a plurality of processors for performing image processing operations on said image data.

a routing table for storing routine data that associates each ultrasound information packet with a subset of said processors according to said location information within that ultrasound information packet;

control circuitry for routine each ultrasound information packet to the subset of processors associated with said ultrasound information packet according to said routing data;

an output bus for transferring processed image data from said plurality of processors to an output device;

a distribution bus coupled to said packetizing circuitry for distributing said ultrasound information packets to said processors; and for each processor, an input buffer coupled to said distribution bus, said control circuitry routing said ultrasound information packet to the subset of processors associated with said ultrasound information packet by instructing the input buffers associated with said subset of processors to read from said distribution bus when said ultrasound information packet is present on said distribution bus, each of said input buffers comprising a ping-pong buffer having a first memory bank and a second memory bank, said ping-pong buffer being adapted to load image data into said first memory bank from said distribution bus while the processor associated with said input buffer is reading image data from said second memory bank, said ping-pong buffer being adapted to load image data into said second memory bank from said distribution bus while said processor is reading image data from said first memory bank;

wherein said ultrasound data is derived from transducer outputs associated with an ultrasound frame, said ultrasound frame comprising at least one zone and a plurality of lines, said location information in said ultrasound information packets comprising:

a zone number corresponding to the zone of the ultrasound frame associated with the image data in said ultrasound information packet, said zone being associated with a depth metric in said ultrasound frame with respect to said transducer; and a line number corresponding to the line of the ultrasound frame associated with the image data in said ultrasound information packet, each ultrasound information packet being routed to said subset of processors based on its line number; and wherein said packetizing circuitry is adapted to organize image data from a single zone within a single line into sequential ultrasound packets, and wherein said control circuitry routes said sequential ultrasound information packets to arrive at said input buffers of said subset of processors in sequential order.

4. The apparatus of claim 3, wherein image data for successive zones of a single line of the ultrasound frame is generated in a non-sequential manner, and wherein said routing table further comprises routing data that associates each ultrasound information packet with an intrabuffer destination address, said intrabuffer destination addresses being assigned such that image data placed into said input buffer memory is automatically rearranged into sequential order when said image data in said ultrasound information packets is stored according to said intrabuffer destination addresses.

5. The apparatus of claim 4, wherein if said bank of memory in said input buffer is input to its associated processor prior to being populated with image data from all lines and zones in said ultrasound frame, said processor is adapted to perform neighborhood interpolation algorithms using image data from known lines and zones to derive estimates of image data from missing zones.

6. A method for processing ultrasound data corresponding to an ultrasound image frame using a plurality of processors, comprising the steps of:
- organizing the ultrasound data into ultrasound information packets according to locations within the ultrasound image frame, said ultrasound information packets comprising location information and corresponding image data;
- for each ultrasound information packet, comparing said location information to a routing table, the routing table comprising routing data that associates each ultrasound information packet with a subset of the plurality of processors according to locations within the ultrasound image frame;
- routing each ultrasound information packet to its associated subset of processors according to said routing data;
- performing image processing algorithms on said image data at the processors; and
- outputting processed image data from the processors onto an output bus for transfer to an output device;
- wherein said step of routing said ultrasound information packet comprises the steps of:
  - placing said ultrasound information packet onto a distribution bus, the distribution bus being coupled to each processor through an input buffer associated with each processor; and
  - instructing the input buffers associated with said subset of processors to read from said distribution bus when said ultrasound information packet is present on said distribution bus;
- wherein each of the input buffers comprises a ping-pong buffer having a first memory bank and a second memory bank, image data being loaded into the first memory bank from the distribution bus while the processor associated with the input buffer is reading, image data from the second memory bank, and image data being loaded into the second memory bank from the distribution bus while the processor is reading image data from said the first memory bank;
- wherein the ultrasound data is derived from transducer outputs associated with an ultrasound frame, the ultrasound frame comprising a plurality of lines, said step of organizing the ultrasound data into ultrasound information packets comprising the step of assigning a line number corresponding to the line of the ultrasound frame associated with the image data in said ultrasound information packet, each ultrasound information packet being routed to its associated subset of processors based on its sector number; and
- wherein the processors are sequentially associated with adjacent sectors of the ultrasound frame, wherein said step of outputting further comprises the step of writing results from an output buffer associated with each processor to the output bus, and wherein the results are written to the output bus in a sequential order corresponding to the adjacent sectors of the ultrasound frame.

7. A method for processing ultrasound data corresponding to an ultrasound image frame using a plurality of processors, comprising the steps of:
- organizing the ultrasound data into ultrasound information packets according to locations within the ultrasound image frame, said ultrasound information packets comprising location information and corresponding image data;
- for each ultrasound information packet, comparing said location information to a routing table, the routing table comprising routing data that associates each ultrasound information packet with a subset of the plurality of processors according to locations within the ultrasound image frame;
- routing each ultrasound information packet to its associated subset of processors according to said routing data;
- performing image processing algorithms on said image data at the processors; and
- outputting processed image data from the processors onto an output bus for transfer to an output device;
- wherein said step of routing said ultrasound information packet comprising the steps of:
  - placing said ultrasound information packet onto a distribution bus, the distribution bus being coupled to each processor through an input buffer associated with each processor; and
  - instructing the input buffers associated with said subset of processors to read from said distribution bus when said ultrasound information packet is present on said distribution bus;
- wherein each of the input buffers comprises a ping-pong buffer having a first memory bank and a second memory bank, image data being loaded into the first memory bank from the distribution bus while the processor associated with the input buffer is reading image data from the second memory bank, and image data being loaded into the second memory bank from the distribution bus while the processor is reading image data from said the first memory bank;
- wherein the ultrasound data is derived from transducer outputs associated with an ultrasound frame, the ultrasound frame comprising a plurality of lines, said step of organizing the ultrasound data into ultrasound information packets comprising the step of assigning a line number corresponding to the line of the ultrasound frame associated with the image data in said ultrasound information packet, each ultrasound information packet being routed to its associated subset of processors based on its sector number;
- wherein said method further comprises the steps of:
  - downloading image processing programs and a routing table from a host computer to and embedded controller over a high-speed serial link;
  - downloading said image processing programs from said embedded controller to said processors; and
  - downloading the routing data from the embedded processor into the routing table;
  - monitoring an operational status of each processor for detecting a malfunctioning processor; and
  - upon detection of a malfunctioning processor, automatically replacing the malfunctioning processor with a spare processor, the spare processor being coupled to the distribution bus and the output bus, the spare processor being coupled to the embedded controller, said step of automatically replacing comprising the steps of:
    - programming the spare processor with a copy of a program being run by the malfunctioning processor; and
    - reloading the routing table such that ultrasound information packets initially directed to the malfunctioning processor prior to the malfunction are directed to the spare processor, whereby image processing functions of the malfunctioning primary processors are automatically redirected to the spare processor.

8. A method for processing ultrasound data corresponding to an ultrasound image frame using a plurality of processors, comprising the steps of:

organizing the ultrasound data into ultrasound information packets according to locations within the ultrasound image frame, said ultrasound information packets comprising location information and corresponding image data;

for each ultrasound information packet, comparing said location information to a routing table, the routing table comprising routing data that associates each ultrasound information packet with a subset of the plurality of processors according to locations within the ultrasound image frame;

routing each ultrasound information packet to its associated subset of processors according to said routing data, performing image processing algorithms on said image data at the processors; and outputting processed image data from the processors onto an output bus for transfer to an output device;

wherein said step of routing said ultrasound information packet comprises the steps of:

placing said ultrasound information packet onto a distribution bus, the distribution bus being coupled to each processor through an input buffer associated with each processor; and instructing the input buffers associated with said subset of processors to read from said distribution bus when said ultrasound information packet is present on said distribution bus;

wherein each of the input buffers comprises a ping-pong buffer having a first memory bank and a second memory bank, image data being loaded into the first memory bank from the distribution bus while the processor associated with the input buffer is reading image data from the second memory bank, and image data being loaded into the second memory bank from the distribution bus while the processor is reading image data from said the first memory bank;

wherein the ultrasound data is derived from transducer outputs associated with an ultrasound frame, the ultrasound frame comprising a plurality of lines, said step of organizing the ultrasound data into ultrasound information packets comprising the step of assigning a line number corresponding to the line of the ultrasound frame associated with the image data in said ultrasound information packet, each ultrasound information packet being routed to its associated subset of processors based on its sector number; and wherein the ultrasound frame further comprises a plurality of zones according to a depth direction, said step of organizing the ultrasound data into ultrasound information packets further comprising the steps of:

assigning a zone number corresponding to the zone of the ultrasound frame associated with the image data in said ultrasound information packet;

organizing image data from a single zone within a single line in the ultrasound frame into sequential ultrasound information packets; and transmitting said sequential ultrasound information packets for routing to the processors;

whereby the sequential ultrasound information packets associated with said single zone within said line in the ultrasound frame arrive at the input buffers of the subset of processors in sequential order.

9. The method of claim 8, wherein image data for successive zones of a single line of the ultrasound frame are generated in a non-sequential manner, and wherein said routing data also associates each ultrasound information packet with an intrabuffer destination address, said intrabuffer destination addresses being assigned such that image data placed into the input buffer memory is automatically rearranged into sequential order when said image data in said ultrasound information packets is stored according to said intrabuffer destination addresses.

10. The method of claim 9, wherein if said memory bank in said input buffer is input to its associated processor prior to being populated with image data from all lines and zones in the ultrasound frame, the processor is adapted to perform neighborhood interpolation algorithms using image data from known lines and zones to derive estimates of image data from missing zones.

11. A computer program product for organizing ultrasound data received from an ultrasound transducer for future processing, comprising:

computer code for receiving a plurality of digital samples corresponding to locations in an ultrasound frame;

computer code for deriving location information corresponding to said plurality of digital samples;

computer code for forming a header comprising said location information;

computer code for forming a payload comprising said digital samples;

computer code for forming an end sequence that signals the end of a packet;

computer code for concatenating said header, payload, and end sequence into an ultrasound information packet; and computer code for distributing each of said ultrasound information packets associated with said ultrasound frame to a subset of a plurality of processors according to its location information, wherein different ultrasound information packets having different location information may be sent to distinct subsets of said plurality of processors;

wherein said locations in the ultrasound frame corresponding correspond to adjacent physical locations along a line within said ultrasound frame, said computer code for deriving location information further comprising:

computer code for deriving the line number within said ultrasound frame associated with said digital samples;

computer code for deriving a zone number within said ultrasound frame associated with said digital samples; and wherein said computer code for deriving said location information is adapted to derive said line numbers and said zone numbers for ultrasound data that is received from the ultrasound transducer in a random line order.

12. The computer program product of claim 11, said computer program product further comprising computer code for organizing image data from a single zone within a single line in the ultrasound frame into sequential ultrasound information packets.

13. A computer-readable storage medium having a configuration that represents routing data for use by an ultrasound information processing system, said ultrasound information processing system having a plurality of processors, said ultrasound information processing system for receiving and processing a stream of ultrasound information packets, said ultrasound packets comprising location information from an ultrasound frame and image data corresponding thereto, said computer-readable storage medium comprising:

- a location table comprising a list of ultrasound frame location identifiers; and
- a destination identifier corresponding to each of said ultrasound frame location identifiers in said location table, said destination identifier identifying a subset of said processors that are to process the image data associated with said ultrasound frame location identifier, said ultrasound information processing system routing said ultrasound information packets to said subset of processors for performing image processing algorithms on said image data and outputting results to an output device;
- wherein the ultrasound frame comprises a plurality of lines, said ultrasound frame location identifiers comprising a line number corresponding to a line of the ultrasound frame, said ultrasound information processing system routing said ultrasound information packets to said subset of processors based on said line number; and
- wherein said ultrasound information frame comprises a plurality of sectors, said sectors comprising a plurality of adjacent lines within said ultrasound frame, wherein said destination identifier identifies a plurality of said processors that are to process the image data associated with said ultrasound frame location identifier, whereby image data from a single line in said ultrasound frame may be processed by more than one processor to allow for spatial image processing operations to be performed on overlapping sectors with reduced edge artifacts and without requiring inter-processor transfer of image data.

14. An apparatus for processing ultrasound data, said ultrasound data comprising ultrasound information packets having ultrasound frame location information and image data corresponding to said ultrasound frame location information, said apparatus comprising:

- receiving circuitry for receiving the ultrasound information packets;
- a plurality of primary processors for performing image processing operations on said image data;
- a spare processor also capable of performing image processing operations on said image data;
- a routing table for storing routing data that associates each ultrasound information packet with a subset of said processors according to the location information within that ultrasound information packet;
- control circuitry for distributing each ultrasound information packet to the subset of processors associated with said ultrasound information packet according to said routing data;
- an embedded controller coupled to said primary processors, said spare processor, said routing table, and said control circuitry, said embedded controller for downloading program data to said primary processors and said spare processor, said embedded controller also for downloading modified routing data to said routing table, said embedded controller being capable of detecting a malfunction of any of said primary processors; and
- an output bus for transferring processed image data from said processors to an output device;
- wherein, upon detection of a malfunction of one of said primary processors, said embedded controller automatically programs said spare processor with a copy of a program being run by said malfunctioning primary processor and reloads said routing table such that ultrasound information packets initially directed to said malfunctioning primary processor prior to the malfunction are directed to said spare processor;
- whereby image processing functions of a malfunctioning primary processors are automatically redirected to said spare processor, thus increasing field reliability of said ultrasound data processing apparatus.

* * * * *